(12) United States Patent
Sako et al.

(10) Patent No.: US 10,466,773 B2
(45) Date of Patent: Nov. 5, 2019

(54) DISPLAY DEVICE AND DISPLAY METHOD THAT DETERMINES INTENTION OR STATUS OF A USER

(71) Applicant: Sony Corporation, Tokyo (JP)

(72) Inventors: Yoichiro Sako, Tokyo (JP); Masaaki Tsuruta, Tokyo (JP); Taiji Ito, Kanagawa (JP); Masamichi Asukai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 142 days.

(21) Appl. No.: 15/652,835

(22) Filed: Jul. 18, 2017

(65) Prior Publication Data

US 2017/0315610 A1    Nov. 2, 2017

Related U.S. Application Data

(63) Continuation of application No. 14/962,429, filed on Dec. 8, 2015, now Pat. No. 9,733,701, which is a
(Continued)

(30) Foreign Application Priority Data

Sep. 8, 2006    (JP) .................................. 2006-244686

(51) Int. Cl.
  *G06F 3/01*    (2006.01)
  *A61B 5/16*    (2006.01)
(Continued)

(52) U.S. Cl.
  CPC ............ *G06F 3/011* (2013.01); *A61B 5/0013* (2013.01); *A61B 5/16* (2013.01); *A61B 5/165* (2013.01);
(Continued)

(58) Field of Classification Search
  CPC ........ G06F 3/011; G06F 19/00; G06F 3/0484; G16H 40/63; A61B 5/0013; A61B 5/742;
(Continued)

(56) References Cited

U.S. PATENT DOCUMENTS 5,734,421 A    3/1998  Maguire, Jr.
5,841,409 A   11/1998  Ishibashi et al.
(Continued)

FOREIGN PATENT DOCUMENTS

CN    1462543    12/2003
EP    0 709 816 A2    5/1996
(Continued)

OTHER PUBLICATIONS

Office Action dated Jun. 30, 2015 in Japanese Patent Application No. 2014-193805.
(Continued)

*Primary Examiner* — Gevell V Selby
(74) *Attorney, Agent, or Firm* — Xsensus, LLP

(57) ABSTRACT

The present invention provides a display apparatus and a display method for realizing control for display operations by a user precisely reflecting the user's status, i.e., the user's intentions, visual state and physical conditions. Worn as an eyeglass-like or head-mount wearable unit for example, the display apparatus of the present invention enables the user to recognize visibly various images on the display unit positioned in front of the user's eyes thereby providing the picked up images, reproduced images, and received images. As control for various display operations such as switching between the display state and the see-through state, display operation mode and selecting sources, the display apparatus of the present invention acquires information about either behavior or physical status of the user, and determines either intention or status of the user in accordance with the
(Continued)

acquired information, thereby controlling the display operation appropriately on the basis of the determination result.

23 Claims, 19 Drawing Sheets

Related U.S. Application Data continuation of application No. 14/481,576, filed on Sep. 9, 2014, now Pat. No. 9,261,956, which is a continuation of application No. 13/614,591, filed on Sep. 13, 2012, now Pat. No. 8,860,867, which is a continuation of application No. 12/438,735, filed as application No. PCT/JP2007/065083 on Aug. 1, 2007, now Pat. No. 8,368,794.

(51) Int. Cl.

| | |
|---|---|
| A61B 5/00 | (2006.01) |
| G02B 27/01 | (2006.01) |
| H04N 7/18 | (2006.01) |
| G06F 3/0484 | (2013.01) |
| G16H 40/63 | (2018.01) |
| A61B 3/11 | (2006.01) |
| A61B 3/12 | (2006.01) |
| A61B 5/01 | (2006.01) |
| A61B 5/021 | (2006.01) |
| A61B 5/024 | (2006.01) |
| A61B 5/053 | (2006.01) |
| A61B 5/08 | (2006.01) |
| A61B 5/11 | (2006.01) |

(52) U.S. Cl.
CPC ............ *A61B 5/6814* (2013.01); *A61B 5/742* (2013.01); *G02B 27/017* (2013.01); *G06F 3/0484* (2013.01); *G16H 40/63* (2018.01); *H04N 7/183* (2013.01); *A61B 3/112* (2013.01); *A61B 3/12* (2013.01); *A61B 5/01* (2013.01); *A61B 5/021* (2013.01); *A61B 5/024* (2013.01); *A61B 5/0533* (2013.01); *A61B 5/0816* (2013.01); *A61B 5/11* (2013.01); *A61B 5/4261* (2013.01); *A61B 2562/0219* (2013.01); *G02B 2027/014* (2013.01); *G02B 2027/0118* (2013.01); *G02B 2027/0138* (2013.01); *G02B 2027/0178* (2013.01); *G02B 2027/0187* (2013.01)

(58) Field of Classification Search
CPC ...... A61B 5/165; A61B 5/6814; H04N 7/183; G02B 27/017
See application file for complete search history.

(56) References Cited

U.S. PATENT DOCUMENTS

| | | | |
|---|---|---|---|
| 5,905,525 A | 5/1999 | Ishibashi et al. | |
| 5,978,015 A | 11/1999 | Ishibashi et al. | |
| 6,091,546 A | 7/2000 | Spitzer | |
| 6,388,638 B2 | 5/2002 | Fukushima et al. | |
| 6,480,174 B1* | 11/2002 | Kaufmann | G02B 27/0172 345/7 |
| 6,549,231 B1 | 4/2003 | Matsui | H04N 7/183 348/151 |
| 6,558,050 B1* | 5/2003 | Ishibashi | G03B 17/00 348/158 |
| 7,233,312 B2* | 6/2007 | Stern | G06F 3/011 345/156 |
| 7,855,743 B2 | 12/2010 | Sako et al. | |
| 2001/0038360 A1 | 11/2001 | Fukushima et al. | |
| 2003/0174211 A1 | 9/2003 | Imaoka et al. | |
| 2003/0234885 A1 | 12/2003 | Pilu | |
| 2005/0190989 A1 | 9/2005 | Kondo et al. | |
| 2005/0248852 A1 | 11/2005 | Yamasaki | |
| 2005/0256675 A1 | 11/2005 | Kurata | |
| 2006/0061544 A1 | 3/2006 | Min et al. | |
| 2006/0158731 A1 | 7/2006 | Eichenlaub | |
| 2006/0170669 A1 | 8/2006 | Walker et al. | |
| 2007/0055888 A1* | 3/2007 | Miller | G06F 21/32 713/186 |
| 2007/0132663 A1 | 6/2007 | Iba et al. | |
| 2007/0159470 A1* | 7/2007 | Jeng | G06F 1/3218 345/204 |
| 2007/0195012 A1 | 8/2007 | Ichikawa et al. | |
| 2008/0062291 A1 | 3/2008 | Sako et al. | |
| 2008/0062297 A1 | 3/2008 | Sako et al. | |
| 2008/0211921 A1 | 9/2008 | Sako et al. | |
| 2010/0013739 A1* | 1/2010 | Sako | G16H 40/63 345/8 |

FOREIGN PATENT DOCUMENTS

| | | |
|---|---|---|
| EP | 0 827 337 A1 | 3/1998 |
| EP | 1 541 966 A1 | 6/2005 |
| JP | H7-255669 | 10/1995 |
| JP | 8-5954 | 1/1996 |
| JP | 8-123979 | 5/1996 |
| JP | 8-126031 | 5/1996 |
| JP | 9-27970 | 1/1997 |
| JP | 9-185009 | 7/1997 |
| JP | H9-218375 | 8/1997 |
| JP | 11-146057 | 5/1999 |
| JP | 11-177907 | 7/1999 |
| JP | 2000-235366 | 8/2000 |
| JP | 2000-284214 | 10/2000 |
| JP | 2000-307715 | 11/2000 |
| JP | U3075971 | 12/2000 |
| JP | 2001-13941 | 1/2001 |
| JP | 2003-76353 | 3/2003 |
| JP | 2003-157136 | 5/2003 |
| JP | 2004-96224 A | 3/2004 |
| JP | 2004-109995 A | 4/2004 |
| JP | 2004-180208 | 6/2004 |
| JP | 2005-172851 | 6/2005 |
| JP | 2005-283154 A | 10/2005 |
| JP | 2005-348382 A | 12/2005 |
| JP | 2006-98820 A | 4/2006 |
| WO | 2002-019728 | 3/2002 |
| WO | 2005-122128 | 12/2005 |

OTHER PUBLICATIONS

Office Action dated Dec. 24, 2014 in Japanese Patent Application No. 2012-254402.

Office Action dated Mar. 12, 2012 in Chinese Patent Application No. 200780031798.4, with Engiish translation.

Office Action dated Jan. 10, 2012 in Taiwanese Patent Application No. 10120023100.

European Office Action dated Feb. 14, 2012 in European Patent Application No. 07 791 763.1.

Japanese Office Action dated Mar. 21, 2012 in Japanese Patent Application No. 2006-244686, filed Sep. 8, 2006.

Supplementary European Search Report dated May 20, 2011 in European Patent Application No. 07791763.1.

Examination and Search Report dated Nov. 23, 2010 in Singaporean Patent Application No. 200901147-9.

Japanese Office Action dated Aug. 21, 2012 in Japanese Patent Application No. 2006-244686.

Combined Office Action and Search Report dated Jul. 18, 2013 in Chinese Application No. 200780031798.4 (with English translation).

Office Action dated Oct. 1, 2013 in Japanese Patent Application No. 2012-254402.

Office Action dated Jun. 24, 2014 in Japanese Patent Application No. 2012-254402, with English translation.

(56) References Cited

OTHER PUBLICATIONS

Summons to Attend Oral Proceedings Pursuant to Rule 115(1) EPC issued in European Application 07791763.1-1020 dated Jun. 26, 2018.

* cited by examiner

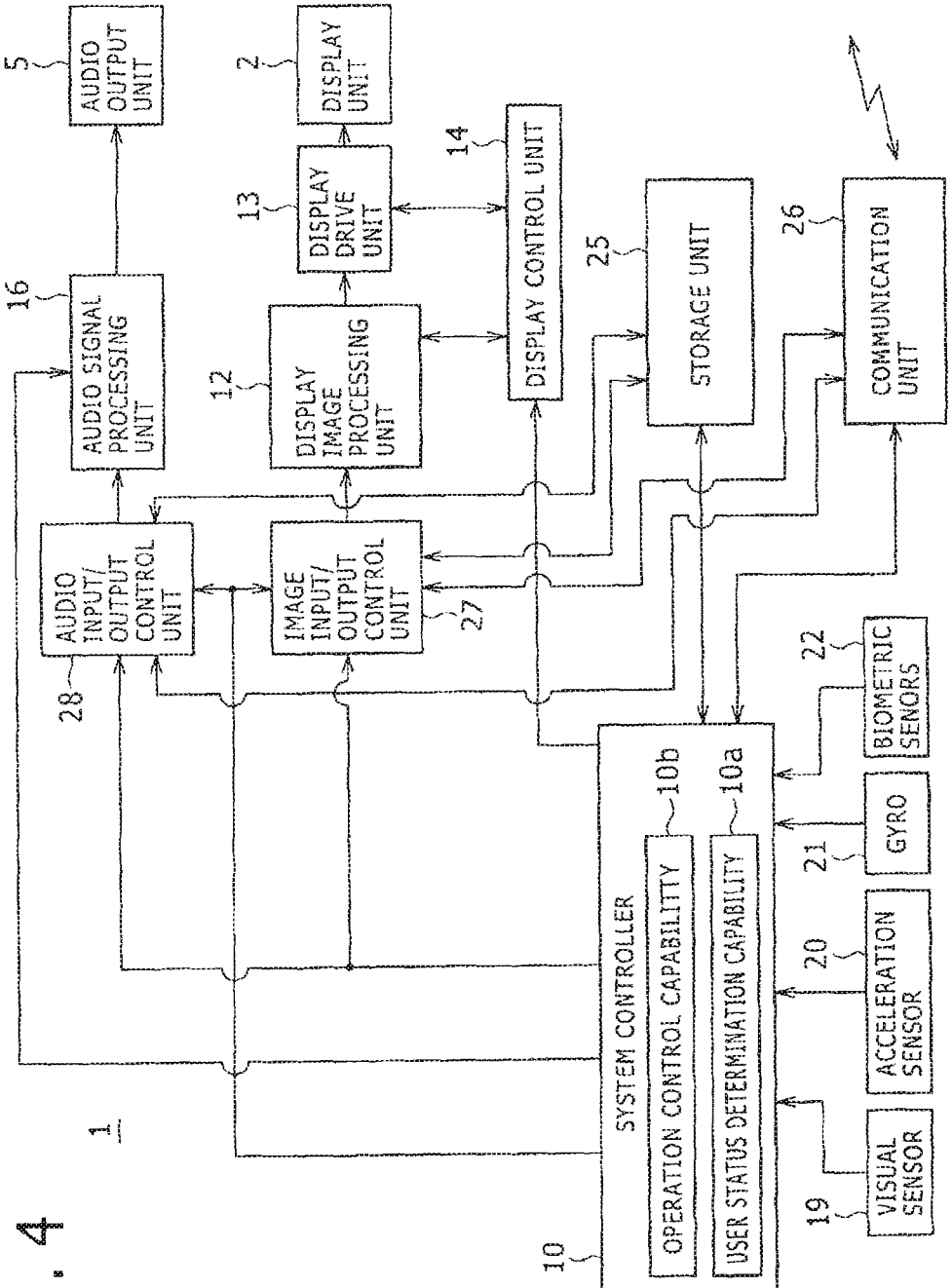

FIG. 6(a) 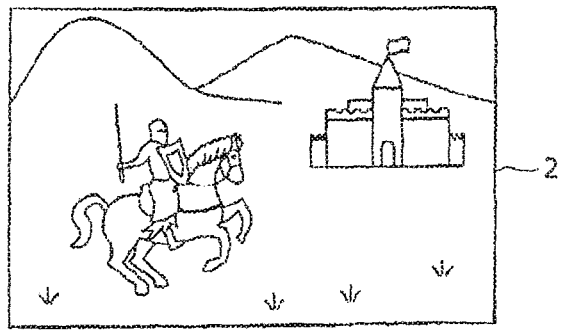

FIG. 6(b) 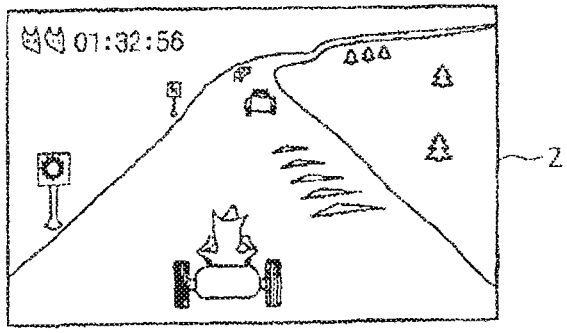

FIG. 6(c)

DESIGNED TO BE WORN BY THE USER, THE DEVICE HAS A TRANSPARENT OR TRANSLUCENT PORTION COVERING THE TEMPLES AND BACK OF THE USER'S HEAD. THIS STRUCTURE ALLOWS THE DEVICE TO PICK UP IMAGES IN THE USER'S LINE OF SIGHT AS THE USER LOOKS AHEAD.
THE DEVICE MAY OUTPUT MOVING IMAGE CONTENTS SUCH AS VIDEO CLIPS, IMAGES FROM DIGITAL STILL CAMERAS, VIDEO GAME IMAGES DERIVED FROM VIDEO GAME PROGRAMS, OR SPREAD-SHEET PROGRAM DATA ILLUSTRATIVELY IN RESPONSE TO THE USER'S PARTICULAR MOVEMENTS SUCH AS THOSE OF THE HEAD, THE WHOLE BODY, ARMS OR LEGS, SUBJECT TO CHECKS ON A TENSE, RELAXED, SUBDUED, SLEEPY, OR OTHER STATE OF THE USER WHERE THESE CAN BE DETECTED. THE DEVICE MAY ALSO BE ACTIVATED BY THE VOLUME OR QUALITY OF THE USER'S VOICE, BY A PREDETERMINED NUMBER OF TIMES THE USER BLINKS (E.G., 3 TIMES), OR BY THE USER STANDING UP TO...

DISPLAY DEVICE AND DISPLAY METHOD THAT DETERMINES INTENTION OR STATUS OF A USER

CROSS-REFERENCE TO RELATED APPLICATIONS

This application is a continuation of U.S. patent application Ser. No. 14/962,429, filed Dec. 8, 2015, which is a continuation of U.S. patent application Ser. No. 14/481,576, filed Sep. 9, 2014 (now U.S. Pat. No. 9,261,956), which is a continuation of application Ser. No. 13/614,591, filed Sep. 13, 2012 (now U.S. Pat. No. 8,860,867), which is a continuation of U.S. patent application Ser. No. 12/438,735, filed Feb. 25, 2009 (now U.S. Pat. No. 8,368,794), which is a national stage of International patent application No. PCT/JP2007/65083, filed Aug. 1, 2007, which claims priority to Japanese patent application No. 2006-244686, filed Sep. 8, 2006. The entire contents of each of which are incorporated herein by reference.

TECHNICAL FIELD

The present invention relates to a display apparatus which is worn by a user as part of an eyeglass-like or head-mount wearable unit and which has display means positioned in front of the user's eyes for image display purposes, as well as to a display apparatus for use with that display apparatus.

BACKGROUND ART

A variety of wearable display apparatuses have so far been proposed, as described illustratively in Japanese Patent Laid-open Nos. Hei 8-126031, Hei 9-27970 and Hei 9-185009. Patent Documents disclose display apparatuses each worn by a user as part of an eyeglass-like or head-mount wearable unit with a display unit located immediately before the user's eyes for image display.

However, traditional display apparatuses such as those cited above have yet to relieve the user of the need to operate their keys or other controls. These apparatuses have yet to offer the kind of display that would suitably reflect the user's intentions and biometric status.

The present invention has been made in view of the above circumstances and provides an apparatus and a method whereby display operations are performed in a manner precisely reflecting the user's status, i.e., his or her intentions and physical conditions.

DISCLOSURE OF THE INVENTION

In carrying out the present invention and according to one embodiment thereof, there is provided a display apparatus including: display means for displaying images as it is positioned in front of the eyes of a user; user information acquisition means for acquiring information about either behavior or physical status of the user; and control means for determining either intention or status of the user in accordance with the information acquired by the user information acquisition means, the control means further controlling display operations of the display means in a manner reflecting the result of the determination.

Preferably, the display apparatus according to an embodiment of the present invention may further include image pickup means for picking up images. In this structure, the control means may preferably control the display means to display image data picked up by the image pickup means in accordance with the information acquired by the user information acquisition means.

Preferably, the display apparatus of the present invention may further include reproduction means for reproducing data from a recording medium. In this structure, the control means may preferably control the display means to display the data reproduced by the reproduction means in accordance with the information acquired by the user information acquisition means. The control means may preferably control reproduction operations of the reproduction means in accordance with the information acquired by the user information acquisition means while the data reproduced by the reproduction means is being displayed by the display unit.

Preferably, the display apparatus according to an embodiment of the present invention may further include reception means for receiving data through communication with an external apparatus. In this structure, the control means may preferably control the display means to display the data received by the reception means in accordance with the information acquired by the user information acquisition means.

Preferably, the display means may be capable of switching between a see-through state and a display state, the see-through state being a state in which the display means remains either transparent or translucent, the display state being a state in which the display means displays supplied data.

The user information acquisition means may preferably be a sensor configured to detect acceleration, angular velocity, or vibration.

The user information acquisition means may preferably be a sensor configured to detect movements of the head, arms, hands, legs, or whole body of the user.

The user information acquisition means may preferably be a sensor configured to detect a stationary state, a walking state, and a running state of the user.

The user information acquisition means may preferably be a visual sensor configured to detect visual information about the user.

The user information acquisition means may preferably be a sensor configured to detect, as visual information about the user, the line of sight, focal distance, pupil dilation, retinal pattern, or blinks of the user.

The user information acquisition means may preferably be a biometric sensor configured to detect biometric information about the user.

The user information acquisition means may preferably be a sensor configured to detect, as biometric information about the user, the heart rate, pulse rate, perspiration, brain wave, galvanic skin reflex, blood pressure, body temperature, or breathing rate of the user.

The user information acquisition means may preferably be a biometric sensor configured to detect information about a tense state or an excited state of the user.

The control means may preferably control the display means to start and end the display operations thereof.

The control means may preferably control the display means to switch between the see-through state and the display state mentioned above.

The control means may preferably control switching between sources which supply data to the display means for display.

The control means may preferably control the display means to scale up and down a display image.

The control means may preferably control the display means to split an onscreen display.

The control means may preferably control the display means to control display brightness.

The control means may preferably control signal processing of an image signal to be displayed by the display means.

The control means may preferably control the display means to scroll images or to feed pages.

The control means may preferably determine an input operation regarding the image displayed by the display means in accordance with the information acquired by the user information acquisition means.

According to another embodiment of the present invention, there is provided a display method for use with a display apparatus having display means for displaying images as it is positioned in front of the eyes of a user, and user information acquisition means for acquiring information about either behavior or physical status of the user, the display method including the steps of: acquiring information about the behavior or physical status of the user; and determining either intention or status of the user in accordance with the information acquired in the information acquiring step, the determining step further controlling display operations of the display means in a manner reflecting the result of the determination.

Where the present invention embodied as outlined above is in use, the inventive display apparatus is worn by the user as part of an eyeglass-like or head-mount wearable unit having display means positioned in front of the user's eyes for visual recognition. Wearing the display apparatus allows the user to view what is being displayed by the display means such as images picked up by image pickup means, images constituted by the data reproduced by reproduction means, or images composed of the data received by reception means of the apparatus.

It is preferred that the display operations be controlled in a manner suitably reflecting the user's intention and status. More specifically, the display operations may involve causing the display means to switch between the display state and the see-through state; selecting sources from which to acquire the image data to be displayed; adjusting diverse display settings such as splitting of the onscreen display, scale-up and scale-down of display images, control of display brightness and other display quality-related attributes, scrolling of images and feeding of pages; inputting data to the display means for display; and causing the display means to display reproduced images. The present invention proposes that these operations be carried out not by the user manipulating switches and controls but by the display apparatus itself acquiring information about the user's behavior or physical status, determining the user's intention or status based on the acquired information, and executing suitable controls in accordance with the result of the determination.

According to an embodiment of the present invention, as outlined above, the display apparatus determines the user's intention or status based on the information about the user's behavior or physical status and controls the display operations accordingly while the display means is displaying images immediately before the user's eyes. This structure permits appropriate display performance reflecting the user's intention or status without bothering the user to manipulate controls or switches. The inventive display apparatus thus provides excellent ease of use for the user while offering varieties of visual experiences.

Since the display means can be placed in the transparent or translucent state as desired, the user can lead normal daily life while continuously wearing the display apparatus. The advantages of the inventive apparatus can thus be exploited by the user while maintaining his or her usual lifestyle.

BRIEF DESCRIPTION OF THE DRAWINGS

FIG. 4 is a block diagram showing another typical structure of the display apparatus.

FIGS. 6a-6c are schematic views explanatory of typical display images retrieved from a storage unit of the display apparatus.

BEST MODE FOR CARRYING OUT THE INVENTION

The display apparatus and display method practiced as preferred embodiments of the present invention will now be described under the following headings:

[1. Appearance of the display apparatus and its relations to external apparatuses]
[2. Typical structure the display apparatus]
[3. Typical displays]
[4. Determination of user status]
[5. Various operations]
[6. Effects, variations and extensions of the embodiments]

Figure 1:
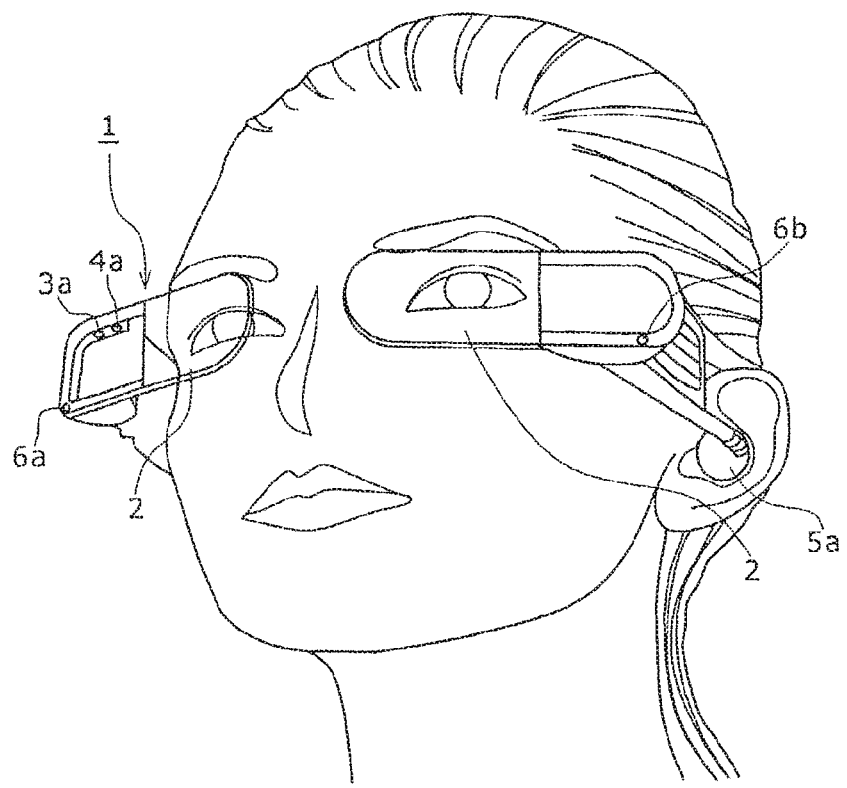
FIG. 1 is a external view explanatory of a display apparatus embodying the present invention.
Figure 2A:
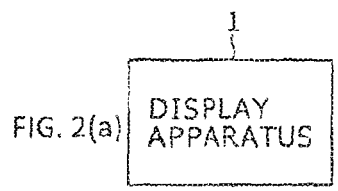
FIGS. 2a-2d are schematic views explanatory of how the inventive display apparatus is typically configured.
Figure 2B:
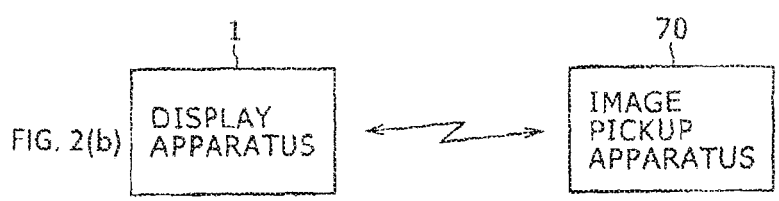
Figure 2C:
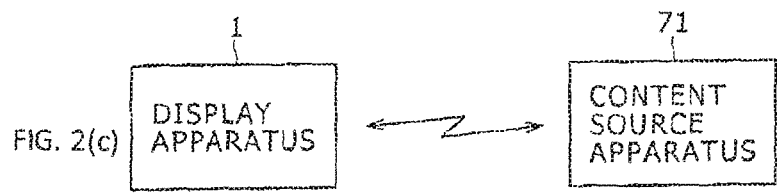
Figure 2D:
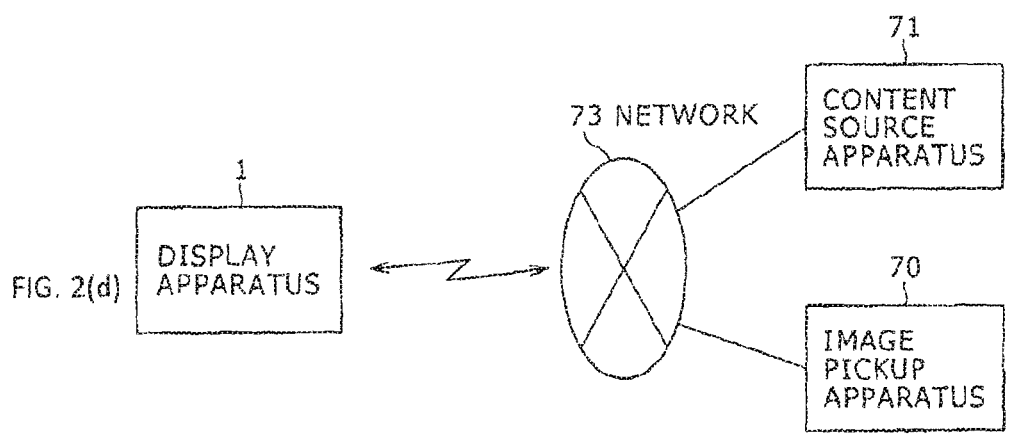

1. Appearance of the Display Apparatus and its Relations to External Apparatuses FIG. 1 shows an external view of a display apparatus 1 embodying the present invention as an eyeglass-like display. The display apparatus 1 typically has a wearable semicircular frame structure which covers the temples and back of a user's head and which is worn by the user in a manner hitched onto his or her ear conches as illustrated.

Worn by the user as shown in FIG. 1, the display apparatus 1 has a pair of display units 2 positioned immediately before the user's eyes, i.e., where the lenses of a pair of eyeglasses would ordinarily be located. The display unit 2 illustratively utilizes a liquid crystal display (LCD) panel of which the permeability is adjusted so as to bring about a see-through state (i.e., transparent or translucent state) as needed. Placed in its see-through state, each display unit 2 poses no impediment to the user's daily life when worn continuously just like eyeglasses.

With the display unit 2 worn by the user, an image pickup lens 3a is oriented forward so as to pick up images of objects in the user's line of sight.

A lighting element 4a is positioned in a manner giving illumination in the direction in which the image pickup lens 3a picks up the images. The lighting element 4a is typically formed by a light-emitting diode (LED).

A pair of earphone-like speakers 5a are furnished to be inserted into the user's ears (only the left-hand side is shown in FIG. 1).

A pair of microphones 6a and 6b for picking up external sounds are positioned at a right-hand edge of the display unit 2 for the right eye and at a left-hand edge of the display unit 2 for the left eye.

What is shown in FIG. 1 is only an example; there may be diverse structures in which the display apparatus 1 may be devised to be worn by the user. Generally, the wearable unit may be of eyeglass type or of head mount type. Any structure is acceptable for the embodiment of the invention as long as the display unit 2 is located in front of and close to the user's eyes. The pair of display units 2 above may be replaced alternatively by a single display unit 2 for one-eye use.

As another alternative, the pair of earphone-like speakers 5a for stereo sound effects may be replaced by a single earphone for one-ear use. Likewise, the pair of microphones 6a and 6b may be replaced by a single microphone.

The structure of FIG. 1 was described above as inclusive of the capability to pick up images.

Alternatively, the structure may dispense with the image pickup function. As another alternative, the display apparatus 1 may be free of microphones and/or earphone-like speakers. As a further alternative, the display apparatus 1 may dispense with the lighting element 4a.

The internal structure of the display apparatus 1, which will be discussed later in detail, may include a reproduction capability (storage unit 25 in FIGS. 3 and 4) for reproducing data from a recording medium and a communication capability (communication unit in FIGS. 3 and 4) for communicating with an external apparatus.

Where these capabilities are implemented, the sources from which to derive data as the images to be displayed by the display unit 2 may include an image pickup capability block, a reproduction capability block, and a communication capability block.

FIG. 2 illustrates how the display apparatus 1 is configured in relation to externally connected apparatuses.

(a) of FIG. 2 shows a case in which the display apparatus 1 is configured for standalone use. In this case, if the display apparatus 1 has the image pickup capability, the image data picked up thereby may be displayed by the display unit 2. If the display apparatus 1 has the reproduction capability, then the image data reproduced from the recording medium may be reproduced by the display unit 2. The data that may be reproduced from the recording medium for display purposes may be of diverse kinds: moving image contents such as movies and video clips; still image contents picked up by digital still cameras or the like and stored on the recording medium; electronic book data; computer use data prepared by the user on his or her PC and recorded to the recording medium, including image data, text data, and spreadsheet data; video game images derived from video game programs recorded on the recording medium; and any other data that may be recorded to the recording medium and reproduced therefrom for display use.

(b) of FIG. 2 shows a case where the display apparatus 1 is configured to have the communication capability communicating with an external image pickup apparatus 70. In this case, the display apparatus 1 receives images (moving/still images) picked up by the image pickup apparatus 70 and causes the display unit 2 to display the received images. The external image pickup apparatus 70 may typically be a video camera or a digital still camera capable of data communication. Alternatively, another display apparatus 1 having the image pickup capability as shown in FIG. 1 may be set up as an external image pickup apparatus arranged to communicate with this display apparatus 1.

The external image pickup apparatus 70 may be of diverse types. It may be an image pickup apparatus in the possession of the user utilizing the display apparatus 1 or an image pickup apparatus owned by an acquaintance of the user of the display apparatus 1. Alternatively, the external image pickup apparatus 70 may be an apparatus set up as part of the facility of an image-providing public service or a piece of equipment established by a private service-offering company, both capable of communicating with the display apparatus 1.

(c) of FIG. 2 shows a case where the display apparatus 1 has the communication capability communicating with an external content source apparatus 71. In this case, the display apparatus 1 receives images (moving/still images) from the content source apparatus 71 and causes the display unit 2 to display the received images.

Typically, the content source apparatus 71 may be an AV (audio visual) apparatus such as a video unit, a TV tuner or a home server; or an information processing apparatus such as a PC (personal computer), PDA (personal digital assistant), or a mobile phone. As in the case above, the content source apparatus 71 may be an apparatus in the possession of the user handling the display apparatus 1, an apparatus owned by an acquaintance of the user, an apparatus set up as part of the facility of a content-providing public service, or a server established by a private content-offering company.

The data sent from the content source apparatus 71 to the display apparatus 1 for display purposes may also be of diverse kinds: moving image contents such as movies and video clips; still image contents picked up by digital still cameras or the like and stored on the recording medium; electronic book data; computer use data prepared by the user on his or her PC and recorded to the recording medium, including image data, text data, and spreadsheet data; video game images derived from video game programs recorded on the recording medium; and any other data that may be available in suitable format for display use.

(d) of FIG. 2 shows a case in which the display apparatus 1 has the communication capability, especially one with a communication access feature which makes use of a network 73 such as the Internet, the capability allowing the display apparatus 1 to communicate with an externally established image pickup apparatus 70 or content source apparatus 71 over the network 73. In this case, the display apparatus 1 receives diverse kinds of data through the network 73 and causes the display unit 2 to display the images of the received data.

2. Typical Structure the Display Apparatus

Figure 3:
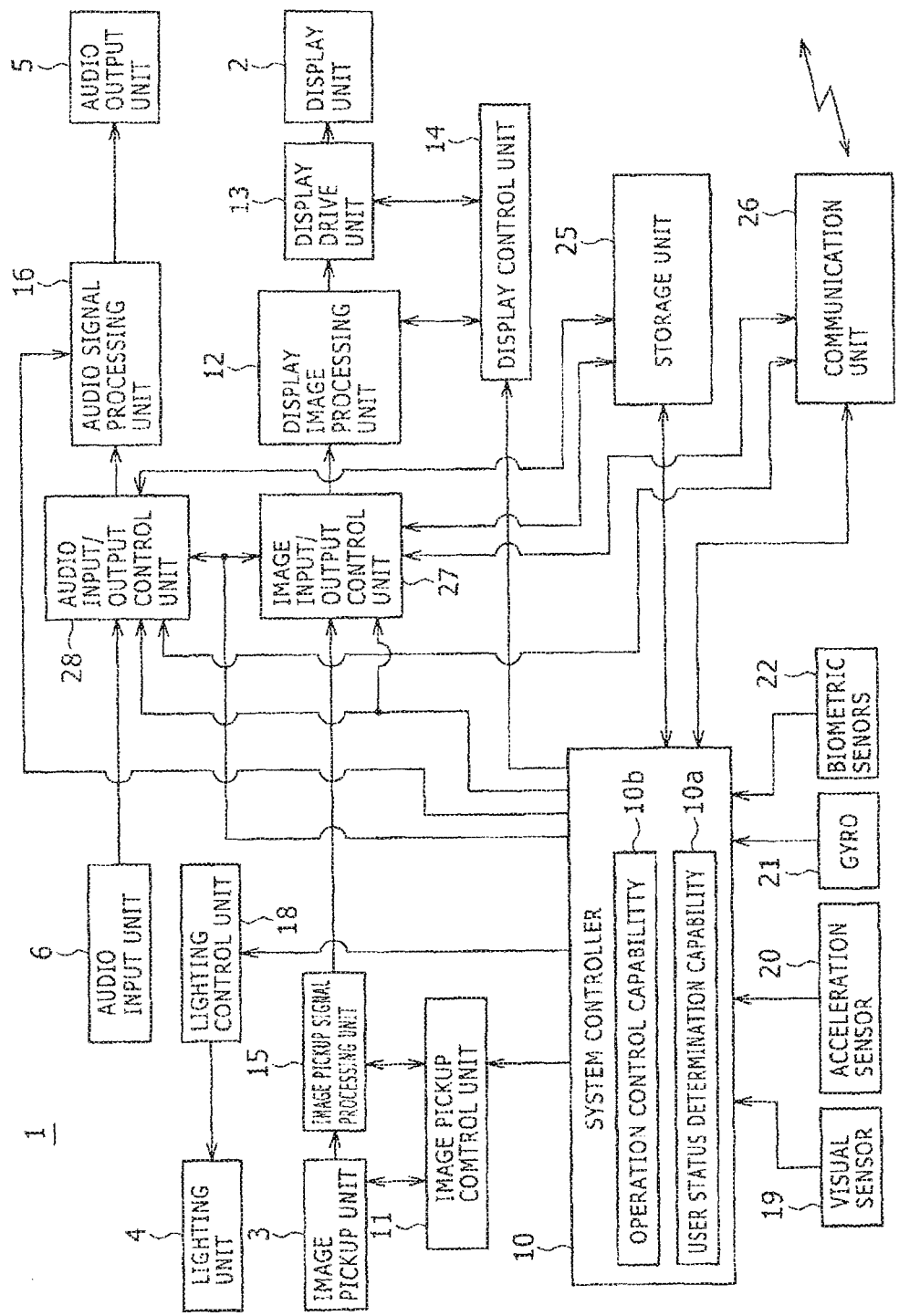
FIG. 3 is a block diagram showing a typical structure of the display apparatus.

FIG. 3 shows a typical internal structure of the display apparatus 1.

A system controller 10 is typically composed of a microcomputer including a CPU (central processing unit), a ROM (read only memory), a RAM (random access memory), a nonvolatile memory, and an interface. In operation, the system controller 10 controls the display apparatus 1 as a whole.

The system controller 10 controls the components of the display apparatus 1 in accordance with the user's status. That is, the system controller 10 runs on a program that detects and determines the user's status and controls the internal components in their operation in a manner reflecting what is detected and determined. In functional terms, the system controller 10 thus has two capabilities: a user status determination capability 10a to determine the user's status, and an operation control capability 10b to give control instructions to the components in accordance with the result of the determination by the user status determination capability 10a, as shown in FIG. 3.

The display apparatus 1 has an image pickup unit 3, an image pickup control unit 11, and an image pickup signal processing unit 15 for picking up images of the scene in front of the user.

The image pickup unit 3 has a lens block, a lens drive block, and a solid state imaging device array. The lens block is made up of the image pickup lens 3a (FIG. 1), an aperture, a zoom lens, and a focus lens. The lens drive block is designed to drive the lenses in focus and zoom operations. The solid state imaging device array detects the light picked up by the lens block and photoelectrically converts the detected light into an image pickup signal. Typically, the solid state imaging device array is a CCD (charge coupled device) sensor array or a CMOS (complementary metal oxide semiconductor) sensor array.

The image pickup signal processing unit 15 includes a video A/D converter, and a sample-and-hold/AGC (automatic gain control) circuit that performs gain control and waveform shaping on the signal acquired by the solid state imaging devices of the image pickup unit 3. Working in this manner, the image pickup signal processing unit 15 obtains an image pickup signal in digital data form. The image pickup signal processing unit 15 also carries out white balance control, brightness control, white signal adjustment, and camera shake correction on the image pickup signal.

Under control of the system controller 10, the image pickup control unit 11 controls the image pickup unit 3 and image pickup signal processing unit 15 in operation. Illustratively, the image pickup control unit 11 controls activation and deactivation of the image pickup unit 3 and image pickup signal processing unit 15. The image pickup control unit 11 also effects motor control on the image pickup unit 3 to regulate auto focusing, automatic exposure, aperture opening, and zoom functions.

The image pickup control unit 11 has a timing generator. Timing signals generated by the timing generator are used to control the solid state imaging devices, as well as the sample-and-hold/AGC circuit and the video A/D converter in the image pickup signal processing unit 11 in their signal processing. Image pickup frame rate can also be controlled as part of the timing control scheme.

Furthermore, the image pickup control unit 11 controls the solid state imaging devices and the image pickup signal processing unit 15 in terms of imaging sensitivity and signal processing. Illustratively, as part of the imaging sensitivity control scheme, gain control is effected on the signal read from the solid state imaging devices. Controls are likewise performed on the black level setting, on coefficients used in image pickup signal processing in the digital data stage, and on the amount of correction in camera shake correction processing. In terms of imaging sensitivity, it is possible to carry out overall sensitivity adjustments regardless of wavebands and to perform sensitivity adjustments taking specific wavebands into consideration such as infrared and ultraviolet ranges. Sensitivity adjustments dependent on wavelengths can be brought about by the introduction of a wavelength filter in the image pickup lens block and by the execution of wavelength filter calculations on the image pickup signal. More specifically, the image pickup control unit 11 can effect sensitivity control by suitably adjusting the wavelength filter being inserted and by designating appropriate filter calculation coefficients.

The image pickup signal (acquired image data) picked up by the image pickup unit 3 and processed by the image pickup signal processing unit 15 is supplied to an image input/output control unit 27.

Under control of the system controller 10, the image input/output control unit 27 controls the transfer of image data, specifically between the image pickup block (image pickup signal processing unit 15), the display block (display image processing unit 12), a storage unit 25, and a communication unit 26.

Illustratively, the image input/output control unit 27 supplies the display image processing unit 12, storage unit 25, and communication unit 26 with the image data constituting the image pickup signal processed by the image pickup signal processing unit 15.

The image input/output control unit 27 also supplies the display image processing unit 12 and communication unit 26 with the image data reproduced illustratively from the storage unit 25.

Furthermore, the image input/output control unit 27 supplies the display image processing unit 12 and storage unit 25 with the image data received illustratively by the communication unit 26.

The display apparatus 1 has the display unit 2, display image processing unit 12, a display drive unit 13, and a display control unit 14 making up the structure for offering displays to the user.

Illustratively, the image data picked up by the image pickup unit 3 and processed by the image signal processing unit 15 as the image pickup signal may be sent to the display image processing unit 12 through the image input/output control unit 27. The display image processing unit 12 is what is generally referred to as a video processor that carries out various display-related processes on the supplied image data. These processes include brightness level adjustment, color correction, contrast adjustment, and sharpness control (edge enhancement) effected on the image data. The display image processing unit 12 is further capable of generation of a partially scaled-up or scaled-down image from the supplied image data, splitting and superimposing of display images based on the supplied image data, generation of characters and graphic images, and superimposing of a generated image onto the supplied image data. That is, the supplied image data can be processed in diverse fashion by the display image processing unit 12.

The display drive unit 13 is constituted by pixel drive circuits that enable the display unit 2 (e.g., LCD) to display the image data supplied from the display image processing unit 12. More specifically, the drive circuits furnish the pixels arranged in matrix fashion in the display unit 2 with drive signals based on video signals occurring at predetermined horizontal and vertical drive timings, whereby the image of the supplied data is displayed. The display drive unit 13 may place the display unit 2 in the see-through state by suitably controlling the transmittance of each of the pixels in the unit 2.

The display control unit 14 controls the display image processing unit 12 in processing and the display drive unit 13 in operation under control of the system controller 10. More specifically, the display control unit 14 causes the display image processing unit 12 to carry out the above-described processes and enables the display drive unit 13 to switch between the see-through state and the image display state.

The image data reproduced from the storage unit 25 or the image data received by the communication unit 26 may be supplied to the display image processing unit 12 via the image input/output control unit 27. In such cases, the reproduced image or the received image is output by the display unit 2 thanks to the above-described workings of the display image processing unit 12 and display drive unit 13.

The display apparatus 1 also includes an audio input unit 6, an audio signal processing unit 16, and an audio output unit 5.

The audio input unit 6 is made up of the microphones 6a and 6b shown in FIG. 1, and of microphone amplifiers and A/D converters for amplifying and converting the audio signals obtained by the microphones 6a and 6b. An audio signal derived from such processing is output as audio data.

The audio data acquired by the audio input unit 6 is supplied to the audio input/output control unit 28.

Under control of the system controller 10, the audio input/output control unit 28 controls transfer of the supplied audio data, specifically the transfer of audio signals between the audio input unit 6, audio signal processing unit 16, storage device 25, and communication unit 26.

For example, the audio input/output control unit 28 supplies the audio data obtained by the audio input unit 6 to the audio signal processing unit 16, to the storage unit 25, or to the communication unit 26.

The audio input/output control unit 28 further supplies the audio data reproduced illustratively from the storage unit 25 to the audio signal processing unit 16 or to the communication unit 26.

The audio input/output control unit 28 also forwards the audio data received illustratively by the communication unit 26 to the audio signal processing unit 16 or to the storage unit 25.

The audio signal processing unit 16 is typically constituted by a digital signal processor and a D/A converter. The audio data obtained by the audio input unit 6 or the audio data coming from the storage unit 25 or from the communication unit 26 is supplied to the audio signal processing unit 16 through the audio input/output control unit 28. Under control of the system controller 10, the audio signal processing unit 16 performs such processes as sound level control, sound quality control, and acoustic effect adjustments on the supplied audio data. The audio data thus processed is converted to an analog signal that is sent to the audio output unit 5. The audio signal processing unit 16 is not limited to the structure for digital signal processing; the unit 16 may also be implemented in a structure including analog amplifiers and analog filters for analog signal processing.

The audio output unit 5 is made up of the above-described pair of earphone-like speakers 5a in FIG. 1 and of amplifier circuits corresponding to the earphone-like speakers 5a.

The audio input unit 6, audio signal processing unit 16, and audio output unit 5 combine to let the user listen to external sounds, to the sounds reproduced from the storage unit 25, or to the sounds received by the communication unit 26. The audio output unit 5 may be structured alternatively as so-called bone conduction speakers.

The storage unit 25 allows data to be written to and read from a suitable recording medium. Typically, the storage unit 25 is implemented as a hard disk drive (HDD). Obviously, the recording medium may be of diverse types including a solid state memory such as a flash memory, a memory card containing a solid state memory, an optical disk, a magneto-optical disk, and a hologram memory. Any of such recording media may be adopted as long as the storage unit 25 can properly write and read data to and from the selected medium.

The image data picked up by the image pickup unit 3 and processed by the image pickup signal processing unit 15 as the image pickup signal, or the image data received by the communication unit 26 can be sent to the storage unit 25 via the image input/output control unit 27. The audio data obtained by the audio input unit 6 or the image data received by the communication unit 26 may be forwarded to the storage unit 25 through the audio input/output control unit 28.

Under control of the system controller 10, the storage unit 25 encodes the supplied image data or audio data preparatory to recording to the recording medium and then writes the encoded data to the recording medium.

The storage unit 25 also reproduces image data or audio data from the recording medium under control of the system controller 10. The reproduced image data is output to the image input/output control unit 27; the reproduced audio data is sent to the audio input/output control unit 28.

The communication unit 26 sends and receives data to and from external apparatuses. Diverse kinds of external apparatuses may communicate with the communication unit 26, including the image pickup apparatus 70 and content source apparatus 71 shown in FIG. 2.

The communication unit 26 may communicate with the external apparatus over a network such as a wireless LAN or a Bluetooth setup with short-distance wireless links to network access points. Alternatively, the communication unit 26 may engage in direct wireless communication with an external apparatus having a suitable communication capability.

The image data picked up by the image pickup unit 3 and processed by the image pickup signal processing unit 15 as the image pickup signal, or the image data reproduced from the storage unit 25 can be sent to the communication unit 26 through the image input/output control unit 27. The audio data acquired by the audio input unit 6 or reproduced from the storage unit 25 can be supplied to the communication unit 26 via the audio input/output control unit 28.

Under control of the system controller 10, the communication unit 26 encodes and modulates the supplied image data or audio data preparatory to transmission, and transmits the data thus processed to the external apparatus.

The communication unit 26 further receives data from the external apparatus. The image data received and demodulated by the communication unit 26 is output to the image input/output control unit 27; the audio data received and demodulated likewise is forwarded to the audio input/output control unit 28.

The display apparatus 1 also includes a lighting unit 4 and a lighting control unit 18. The lighting unit 4 is made up of the lighting element 4a shown in FIG. 1 and a lighting circuit for causing the lighting element 4a (e.g., LED) to emit light. The lighting control unit 18 causes the lighting unit 4 to perform light-emitting operation under control of the system controller 10.

With the lighting element 4a of the lighting unit 4 positioned in a manner giving illumination in the forward direction, the lighting unit 4 provides illumination in the user's line of sight.

The display apparatus 1 further includes a visual sensor 19, an acceleration sensor 20, a gyro 21, and biometric sensors 22 constituting the structure for acquiring user information.

The visual sensor 19 detects information about the user's vision. Illustratively, the visual sensor 19 is capable of detecting such sight-related information as the line of sight, focal distance, pupil dilation, retinal pattern, and blinks of the user.

The acceleration sensor 20 and gyro 21 output signals reflecting the user's movements. Illustratively, these sensors detect the movements of the user's head, neck, whole body, arms, and legs.

The biometric sensors 22 detect biometric information about the user. Illustratively, the biometric sensors 22 detect the heart rate, pulse rate, perspiration, brain wave, galvanic skin reflex (GSR), blood pressure, body temperature, and breathing rate of the user. The signals detected by the biometric sensors 22 constitute information by which to determine the user's diverse states: a tense state, an excited state, a calm state, a sleepy state, or a comfortable state, or an uncomfortable state.

The visual sensor 19, acceleration sensor 20, gyro 21, and biometric sensors 22 combine to acquire information about the user wearing the display apparatus 1 in connection with the user's behavior or physical status. The user information thus acquired is supplied to the system controller 10.

By operating its user status determination capability 10a, the system controller 10 determines the user's intention or status reflecting the acquired user information. With the user's intention or status thus determined, the system controller 10 controls display-related operations through the processing of its operation control capability 10b. More specifically, the system controller 10 instructs the display control unit 14 to control the display image processing unit 12 and display drive unit 13 in operation, selects the source from which to obtain the data to be displayed, or controls the storage unit 25 in reproduction or the communication unit 26 in communication.

Although the visual sensor 19, acceleration sensor 20, gyro 21 and biometric sensors 22 were shown to constitute the structure for acquiring user information, the installation of all these components is not requisite. Other sensors may be added as well, including a voice sensor for detecting the user's voice and a lip-reading sensor for reading the user's lip movements.

FIG. 4 shows a typical structure of the display apparatus 1 minus the image pickup capability. In FIG. 4 as well as in FIG. 3, like reference numerals designate like or corresponding functional block elements, and their descriptions will be omitted where redundant from the ensuing description.

The structure in FIG. 4 is basically the same as that in FIG. 3 minus the image pickup unit 3, image pickup signal processing unit 15, image pickup control unit 11, lighting unit 4, lighting control unit 18, and audio input unit 6.

In the structure of FIG. 3, there are three sources from which to tap the data for display on the display unit 2: the image pickup capability block (image pickup unit 3, image pickup signal processing unit 15, image pickup control unit 11), reproduction capability block (storage unit 25), and reception capability block (communication unit 26). By contrast, the structure of FIG. 4 has two sources that may supply data for display on the display unit 2: the reproduction capability block (storage unit 25), and reception capability block (communication unit 26).

In other words, the setup of FIG. 3 has three display image sources in the display apparatus 1, while the setup of FIG. 4 contains two display image sources inside the display apparatus 1.

Although not shown, other structures than those in FIGS. 3 and 4 may be devised, each containing a different number or different types of display image sources in the display apparatus 1. For example, an alternative structure may be furnished with only the image pickup capability block; another structure with only the reproduction capability block; a further structure with the reception capability block; an even further structure with both the image pickup capability block and the reproduction capability block; and a still further structure with the image pickup capability block and reception capability block.

3. Typical Displays

The system controller 10 controls display-related operations in response to the user's intention or status, selecting the source that supplies the data to be displayed and carrying out processes on display images. This allows the user to view diverse forms and contents of displays on the display unit 2. FIGS. 5 through 10 show typical displays.

Figure 5A:
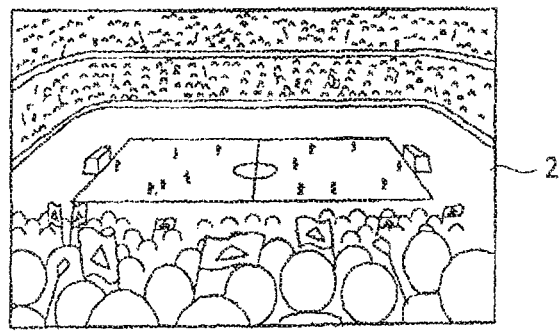
FIGS. 5a-5c are schematic views explanatory of a see-through state and an image display state in which the display apparatus may be placed.
Figure 5B:
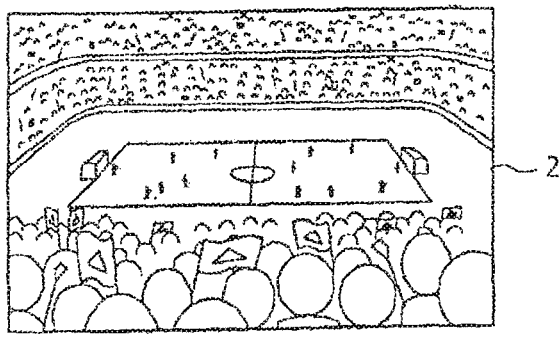
Figure 5C:
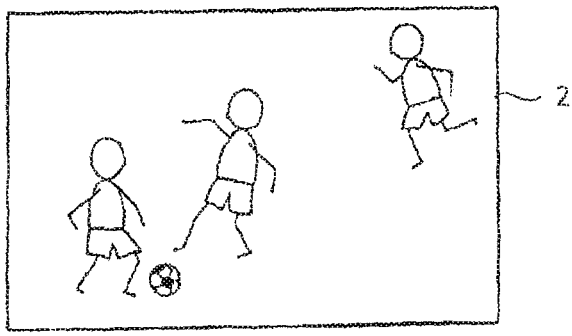

(a) of FIG. 5 shows a case in which the display unit 2 is placed in the see-through state. In this case, the display unit 2 simply acts as a transparent plate member through which the user views the actual scene in front.

(b) of FIG. 5 shows a case where the display unit 2 displays the image picked up by the image pickup unit 3. In this case, illustratively with the user in the state of (a) of FIG. 5 above, the image pickup unit 3, image pickup signal processing unit 15, display image processing unit 12, and display drive unit 13 work to get the display unit 2 displaying a picked-up image. The image displayed by the display unit 2 (normally picked-up image) this time is approximately the same as that in the see-through state. That is, the user is viewing the normal field of vision provided by the image being picked up.

(c) of FIG. 5 shows a case in which the system controller 10 controls the pickup image control unit 11 to get the image pickup unit 3 picking up a telephoto image. The telephoto image thus obtained is displayed by the display unit 2.

Although not shown, if the system controller 10 causes the image pickup control unit 11 to get the image pickup unit 3 picking up a wide-angle shot image, then that wide-angle shot will be displayed by the display unit 2. Switchover between telephoto and wide-angle shot settings may be effected either by controlling the zoom lens drive in the image pickup unit 3 or by getting the image pickup signal processing unit 15 suitably processing signals.

(b) and (c) of FIG. 5 show cases where the image pickup capability block acts as the image source that supplies the display image data to be displayed by the display unit 2. By contrast, FIG. 6 shows cases in which the storage unit 25 acts as the display image source that supplies display image data for display on the display unit 2.

More specifically, (a) of FIG. 6 shows a case where the storage unit 25 retrieves moving or still image contents from its recording medium and has the retrieved contents displayed by the display unit 2.

(b) of FIG. 6 shows a case in which the storage unit 25 has a video game program activated from its recording medium and allows the image data coming from the program to be displayed by the display unit 2.

(c) of FIG. 6 shows a case where the storage unit 25 has electronic book contents retrieved from its recording medium and enables the retrieved contents to be displayed by the display unit 2.

In each of the cases of (a), (b) and (c) of FIG. 6 above, the user can enjoy image data reproduced from the recording medium through the use of the display apparatus 1.

Figure 7A:
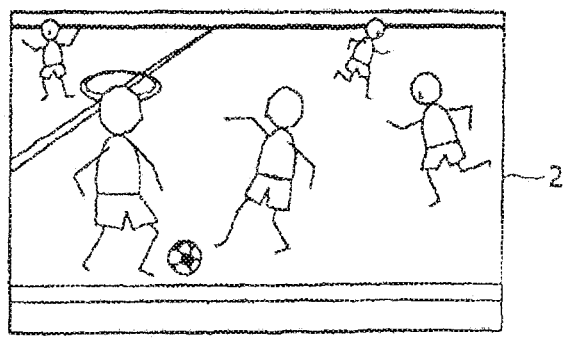
FIGS. 7a-7c are schematic views explanatory of typical display images coming from a communication unit of the display apparatus.
Figure 7B:
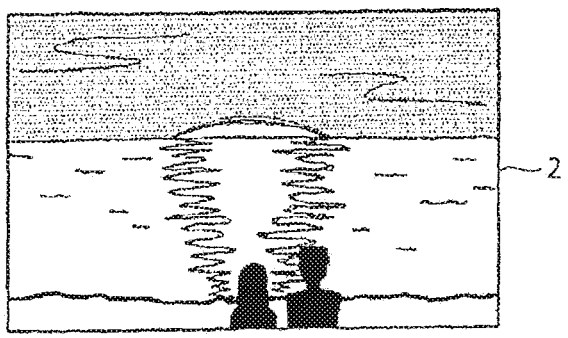
Figure 7C:
Figure 8A:
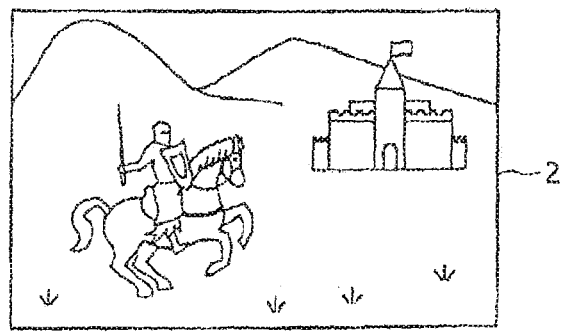
FIGS. 8a-8c are schematic views explanatory of other display images coming from the communication unit of the display apparatus.
Figure 8B:
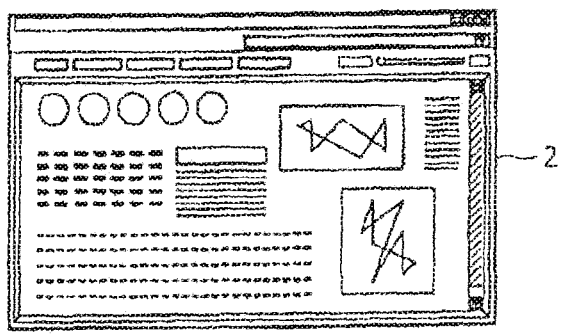
Figure 8C:
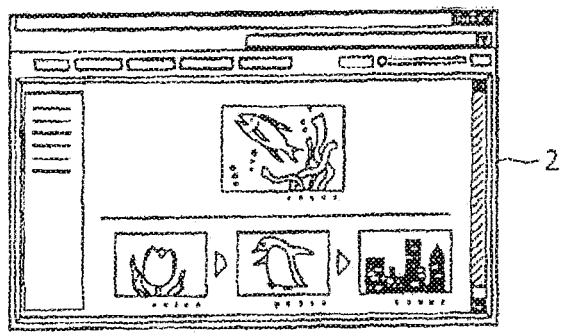

FIGS. 7 and 8 show cases where the communication unit 26 acts as the image source that supplies display image data for display on the display unit 2.

FIG. 7 gives cases where the configuration of (b) of FIG. 2 or (d) of FIG. 2 is in effect and where the display unit 2 displays the image data sent from the external image pickup apparatus 70 and received by the communication unit 26.

More specifically, (a) of FIG. 7 shows a case in which, with the user in the situation of (a) of FIG. 5 watching a soccer game at a stadium, the display unit 2 displays the image picked up by an image pickup apparatus 70 positioned somewhere else in the same stadium and received by the communication unit 26. In this case, the user can watch the game with more interest by getting the display unit 2 displaying images obtained by the image pickup apparatus 70 located close to the team manager's seat or images collected by a miniature image pickup apparatus 70 worn by the referee.

(b) of FIG. 7 shows a case in which the display unit 2 displays the image picked up by an image pickup apparatus 70 set up at a resort or by an image pickup apparatus carried by an acquaintance going on a tour and received by the communication unit 26. In this case, the user can enjoy scenes of diverse regions or countries while at home.

(c) of FIG. 7 shows a case in which the display unit 2 displays a terrestrial view (bird's-eye view) picked up by an image pickup apparatus 70 mounted on aircraft or on a satellite and received by the communication unit 26. In this case, the user can enjoy scenes not encountered in daily life.

FIG. 8 shows cases where the configuration of (c) of FIG. 2 or (d) of FIG. 2 is in effect and where the display unit 2 displays the image data sent from the external content source apparatus 71 and received by the communication unit 26.

More specifically, (a) of FIG. 8 shows a case in which the display unit 2 displays image contents such as moving or still images received from the content source apparatus 71 such as an AV apparatus or a personal computer.

(b) of FIG. 8 shows a case in which the content source apparatus 71 such as a personal computer sends to the display apparatus 1 image data constituting an onscreen display of a website accessed by a browser program of the apparatus 71 or image data making up the display of an application program being active on the apparatus 71. The display apparatus 1 then has the image data received by the communication unit 26 and displayed by the display unit 2.

(c) of FIG. 8 shows a case in which the content source apparatus 71 such as a personal computer sends to the display apparatus 1 image data constituting the display of a list of photos or the like viewed on the apparatus 71. The display apparatus 1 then has the image data received by the communication unit 26 and displayed by the display unit 2.

In the preceding cases, the content source apparatus 71 is typically one of AV apparatuses including video players or an information processing apparatus such as a personal computer. The display apparatus 1 receives and displays the image data sent from any of these content source apparatuses 71. The user wearing the display apparatus 1 can then verify the displayed images and perform various operations accordingly.

FIG. 6 shows cases where the storage unit 25 acts as the source of incoming image data, whereas FIG. 8 indicates cases where the communication unit 26 serves as the image data source. Alternatively, the images shown in FIG. 8 may be considered to be reproduced images coming from the storage unit 25. As another alternative, the images indicated in FIG. 6 may be regarded as images that have been sent from the external apparatus and received by the communication unit 26.

Figure 9A:
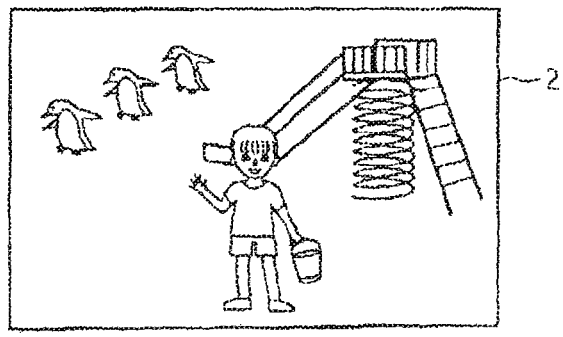
FIGS. 9a-9c are schematic views explanatory of how onscreen displays are split by the display apparatus.
Figure 9B:
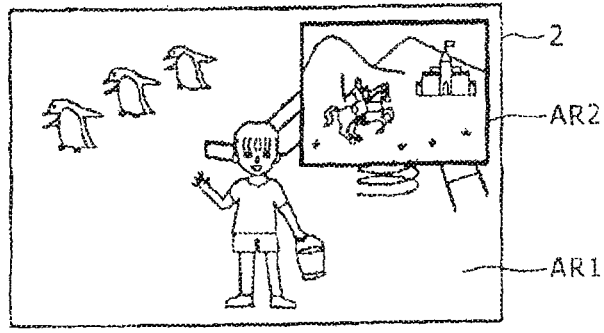
Figure 9C:
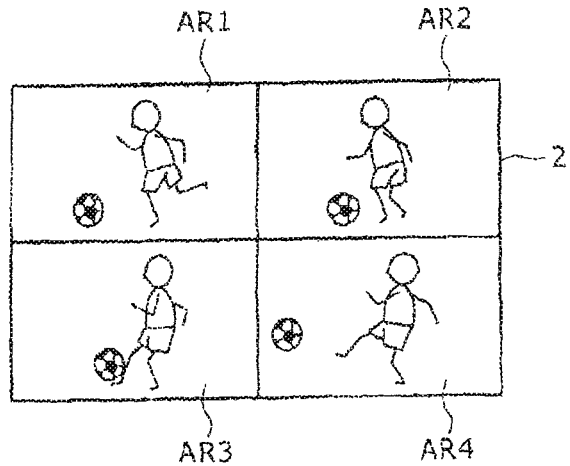
Figure 10A:
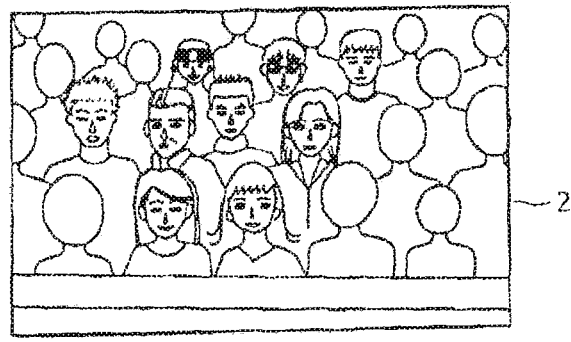
FIGS. 10a-10b are schematic views explanatory of how an image is scaled up when displayed.
Figure 10B:
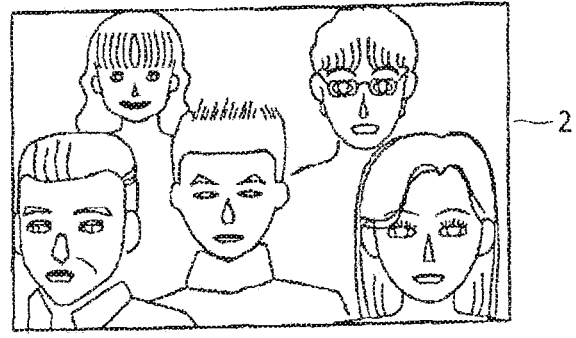
Figure 11A:
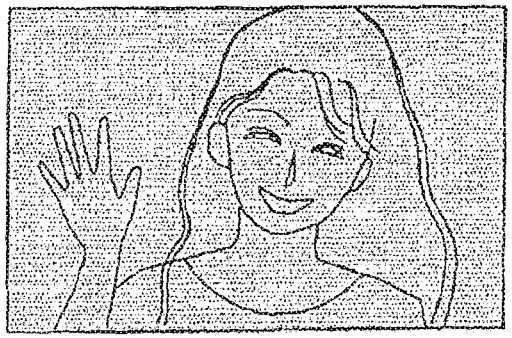
FIGS. 11a-11b are schematic views explanatory of how the brightness of a display image is adjusted.
Figure 11B:

FIGS. 9, 10 and 11 show cases in which images from the above-described diverse sources (image pickup capability block, reproduction capability block, and reception capability block) are processed in terms of display form or in image data format.

(a) of FIG. 9 shows a case where the display unit 2 is placed in the see-through state.

(b) of FIG. 9 shows a case in which the display unit 2 displays split-screen images, with the system controller 11 giving a split-display instruction to the display control unit 14 (display image processing unit 12, display drive unit 13). Illustratively, the onscreen display of the display unit 2 may be split into areas AR1 and AR2. The area AR1 may be in the see-through state or in the normal image display state, while the area AR2 may display images coming from the storage unit 25 or communication unit 26 acting as the source (the images may be reproduced or received video content images).

(c) of FIG. 9 shows another example of the split-screen display. In this case, the screen of the display unit 2 is illustratively split into four areas AR1, AR2, AR3 and AR4, each area displaying one of the frames extracted at predetermined intervals from the image of interest. Illustratively, the display image processing unit 12 is arranged to extract image data on a frame by frame basis at intervals of 0.5 seconds. The extracted image frames are displayed in cyclical fashion from AR1 to AR2 to AR3 to AR4 to AR1 to AR2, and so on. This is an example of images picked up typically under strobe lighting for split-screen display on the display unit 2.

Obviously, it is also possible for each of a plurality of areas making up the screen to display an image from each of different sources.

(a) of FIG. 10 shows a case where an image from the image pickup capability block, reproduction capability block, or reception capability block is displayed in normal size.

If the system controller 10 gives an image scale-up instruction to the display image processing unit 12 through the display control unit 14, then the display unit 2 may display a scaled-up image such as one shown in (b) of FIG. 10.

(a) of FIG. 11 shows a case in which an image coming from the image pickup capability block, reproduction capability block, or reception capability block is displayed as picked up.

This is an image at a low brightness level and it may not be easy for the user to watch it comfortably.

In such a case, the system controller 10 may instruct the display control unit 14 (display image processing unit 12, display drive unit 13) to increase brightness, adjust contrast, and/or enhance sharpness, thereby causing the display unit 2 to display a brighter, clearer image such as one shown in (b) of FIG. 11.

The foregoing displays are merely examples and are not limitative of the present invention. Many other forms of displays can be implemented by the embodiment of the invention. Specifically, such displays are brought about by selecting the source out of the image pickup capability block, reproduction capability block, and reception capability block as desired; by suitably controlling the image pickup capability block or reproduction capability block in operation; or by properly controlling the display image processing unit 12 or display drive unit 13 in terms of processing or in operation.

Illustratively, if the image pickup capability block is selected as the display image source, then it is possible to implement the following displays: telephoto view display, wide-angle view display, zoom-in and zoom-out displays shifting from telephoto to wide-angle settings or vice versa, scale-up display, scale-down display, display at variable frame rates (e.g., images picked up at high or low frame rates), high intensity display, low intensity display, variable contrast display, variable sharpness display, display at enhanced imaging sensitivity, display at enhanced infrared imaging sensitivity, display at enhanced ultraviolet imaging sensitivity, and display of images with their specific wavebands suppressed.

If the reproduction capability block or reception capability block is selected as the display image source, then it is possible to implement displays of images reproduced at varied speeds such as high-speed reproduction, slow reproduction, frame-by-frame advance reproduction; as well as changing of pages being displayed or scrolling of images as is carried out on a personal computer or the like.

Where the display image processing unit 12 is suitably controlled in terms of processing, it is conceivable to implement displays with diverse onscreen effects, such as images with pixelated mosaic effect, images in reverse video, soft-focus images, partially highlighted images, and images in varied ambient colors.

4. Determination of User Status

As described above, the display apparatus 1 embodying the present invention has the visual sensor 19, acceleration sensor 20, gyro 21, and biometric sensors 22 constituting the structure for acquiring user information.

The visual sensor 19 is used to detect information about the user's sight. For example, the visual sensor 19 may be formed by an image pickup arrangement located close to the display unit 2 to take pictures of the user's eyes. Images of the user's eyes are picked up by that image pickup arrangement and acquired by the system controller 10 wherein the user status determination capability 10a analyses the obtained images. The analysis provides information about the line of sight, focal distance, pupil dilation, retinal pattern, and blinks of the user. The information thus acquired is used as the basis for determining the user's status or intentions.

Alternatively, the visual sensor 19 may be formed by a light-emitting arrangement and a light-receiving arrangement, the light-emitting arrangement being located close to the display unit 2 and emitting light to the user's eyes, the light-receiving arrangement receiving reflected light from the user's eyes. Illustratively, the thickness of the user's crystalline lens is detected from a received-light signal. The detected lens thickness in turn serves as the basis for detecting the focal distance of the user's eye.

By detecting the user's line of sight, the system controller 10 can determine which part of the image displayed illustratively by the display unit 2 is attracting the user's attention.

It is also possible for the system controller 10 to recognize the user's line of sight as an input operation. For example, the user's line of sight being moved rightward or leftward may be interpreted as instructions input to the display apparatus 1.

By detecting the user's focal distance, it is possible to determine whether the scene currently attracting the user's attention is nearby or far away. This in turn permits execution of zoom control and scale-up/scale-down control. Illustratively, the user's act of looking at a distant object may be interpreted as a cue to bring about a telephoto view display.

By detecting the degree of the user's pupil dilation, it is possible to determine how the user is reacting to glare of the ambient brightness if the see-through state is in effect or to glare of the onscreen image brightness if the monitor display state is in use. According to the user's reaction thus determined, the system controller 10 may control brightness and imaging sensitivity.

The user's retinal pattern may be detected illustration for use in authenticating the user's identity. Since every person has his or her unique retinal pattern, the user wearing the display apparatus is identified so that the apparatus may be controlled in a manner suitable for the detected identity. Alternatively, the display apparatus may enable its monitor to be operated only for a specifically authenticated user.

By detecting the user's blinks, it is possible to determine the degree of the user's eyestrain due to glare or other causes. It is also possible to interpret the user's blinks as input operations deliberately executed by the user. For example, three consecutive blinks made by the user may be interpreted as a cue to bring about a particular operation.

The acceleration sensor 20 and gyro 21 output signals corresponding to the user's movements. Illustratively, the acceleration sensor 20 is suitable for detecting linear movements while the gyro 21 is suited to sense rotary or vibratory motions.

When appropriately positioned on the user's body, the acceleration sensor 20 and gyro 21 can detect movements of the user's whole body or body parts.

For example, the acceleration sensor 20 and gyro 21 may be mounted inside the eyeglass-like display apparatus 1 shown in FIG. 1 so as to detect movements of the user's head. In this case, the acceleration sensor 20 provides information about the acceleration of the user's head or whole body, and the gyro 21 yields information about the angular velocity and vibration of the user's whole body.

The above sensor setup primarily detects the user's behavior in terms of head or neck movements. Illustratively, the sensors can detect whether the user is looking upward or downward. The user's head directed downward may be interpreted to mean that the user is looking at a nearby object like a book as in reading; the user's head oriented upward may be interpreted to signify that the user is looking at a faraway object.

Upon detecting the user shaking his or her head, the system controller 10 can interpret the motion as the user's deliberate action. For example, if the user is found to shake his head twice leftward, the action may be recognized as a particular input operation.

The acceleration sensor 20 and gyro 21 may be suitably arranged to detect whether the user is at rest (stationary), is walking, or is running. It is also possible for these sensors to determine whether the user has sat down from his or her standing position or has now stood up from the sitting position.

As another alternative, the acceleration sensor 20 and gyro 21 may be attached to the user's arms or legs apart from the wearable unit mounted on the user's head. This sensor setup makes it possible to detect movements of only the arms or the legs of the user.

The biometric sensors 22 are designed to detect information about the heart rate, pulse rate, perspiration, brain wave (e.g., alpha wave, beta wave, theta wave, gamma wave), galvanic skin reflex, body temperature, blood pressure, and breathing (e.g., rate and depth of breathing, amount of ventilation) of the user. These items of information, when acquired, allow the system controller 10 to detect whether the user is in a tense state, an excited state, a calm state, a comfortable state, or an uncomfortable state.

Whether or not the display apparatus 1 is currently worn by the user may be determined based on biometric information, and this information may be used for operational purposes. Illustratively, if the display apparatus 1 is found unmounted by the user, then the system controller 10 may place the apparatus 1 in standby mode in which checks are made only for biometric information. As soon as the display apparatus 1 is found worn by the user, the system controller 10 may activate the apparatus 1. When the user is found to have unmounted the display apparatus 1, the system controller 10 may place the apparatus 1 back into standby mode.

The information detected by the biometric sensors 22 may also be utilized for authentication of the user's identity (so that the apparatus should be worn by the properly identified person).

The biometric sensors 22 may be located inside the head mount frame of the eyeglass-like display apparatus 1. Illustratively, the information described above may be derived from the temples and back of the user's head. Alternatively, the biometric sensors 22 may be positioned elsewhere on the user's body, independent of the head mount frame of the display apparatus 1.

5. Various Operations

As described above, the display apparatus 1 embodying the present invention has its system controller 10 control display-related operations in accordance with the user information detected by the visual sensor 19, acceleration sensor 20, gyro 21, and biometric sensors 22. In this manner, the system controller 10 allows the display unit 2 to display images that reflect the user's intention and status and are thus fit for his or her preferences.

Such operations carried out under control of the system controller 10 will now be described below.

Figure 12:
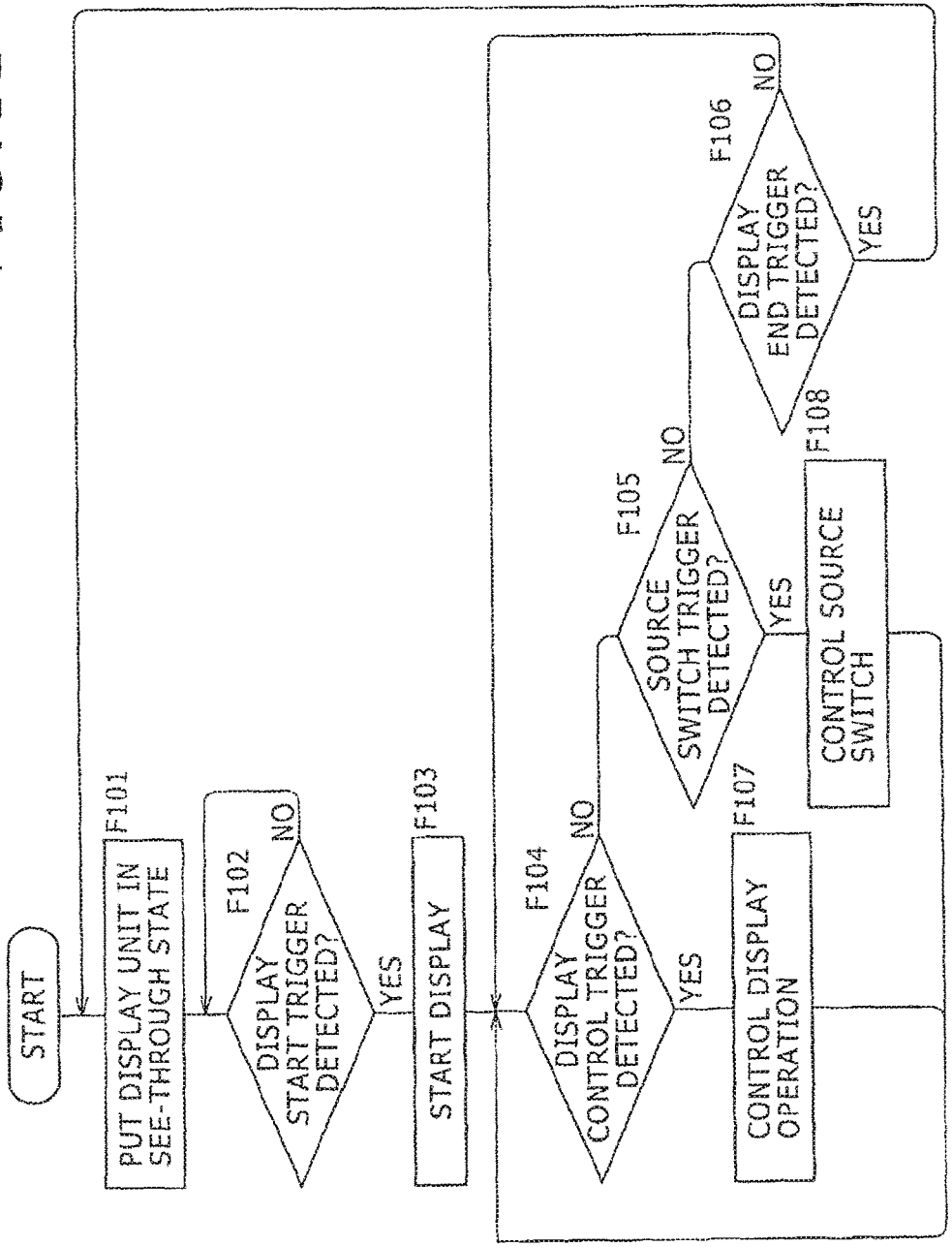
FIG. 12 is a flowchart of steps constituting a typical control process performed by the display apparatus.

FIG. 12 is a flowchart of steps constituting a typical control process performed by the operation control capability 10b of the system controller 10.

In step F101, the system controller 10 controls the display control unit 14 to place the display unit 2 in the see-through state. Illustratively, when the display apparatus 1 is initially switched on, the system controller 10 goes to step F101 and puts the display unit 2 in the see-through state.

With the display unit 2 in the see-through state, the system controller 10 goes to step F102 and checks to determine whether a display start trigger is detected. The display start trigger signifies an event that cues the system controller 10 in causing the display unit 2 to start its display operation in view of the user's intention or status determined by the user status determination capability 10a. The system controller 10 recognizes a specific display start trigger in the form of the user's explicit operation, user's deliberate act (i.e., action interpreted as an operation), or the user's unconscious movement or status (including the user's perception). Some examples of the trigger are described below.

If a display start trigger is detected, then the system controller 10 goes to step F103 and controls the start of display. More specifically, the system controller 10 instructs the display control unit 14 to control the display image processing unit 12 and display drive unit 13 in order to have the display unit 2 display supplied data as a normal pickup image.

The display image processing unit 12 is supplied with image data through the image input/output control unit 27. If a plurality of image data sources exist as shown in FIG. 3 or 4, then the display image processing unit 12 may be fed at this point with the image data from the image pickup capability block (image pickup unit 3, image pickup signal processing unit 15), reproduction capability block (storage unit 25), or reception capability block (communication unit 26), whichever is selected by default. Illustratively, if the image pickup capability block is selected by default as the source, then the system controller 10 reaching step F103 instructs the image pickup control unit 11 to start picking up images, causes the image pickup unit 3 and image pickup signal processing unit 15 to perform normal image pickup operation, and sends the image data constituting an image pickup signal to the display image processing unit 12 through the image input/output control unit 27. In this case, the display unit 2 is typically switched from the see-through state of (a) of FIG. 5 to the monitor display state effecting a normal pickup image as shown in (b) of FIG. 5.

If the default source is the storage unit 25, then the system controller 10 in step F103 may start up the storage unit 25 and get the display unit 2 to display reproduced contents or a menu screen for selection of contents coming from the storage unit 25. If the default source is the communication unit 26, then the system controller 10 in step F103 may start up the communication unit 26 and get the display unit 2 to display a communication-ready screen or images of data received from an external apparatus.

Obviously, if there is one source, the image data from that source need be supplied to the display image processing unit 12.

As another alternative, when step F103 is reached in which to control the start of display, the display unit 2 may be arranged to display a menu screen or a source selection screen as its initial screen, with no image data supplied from image sources.

Although the process of FIG. 12 contains no particular mention of audio output from the audio output unit 5, it is assumed that during the display operation by the display unit 2, the system controller 10 controls the audio input/output control unit 28 and audio signal processing unit 16 to output sounds based on the audio data from the same source that supplies display images.

While the image coming from a given source is being displayed by the display unit 2, the system controller 10 goes to step F104 and checks to determine whether a display control trigger has occurred. If no display control trigger is detected, then the system controller 10 goes to step F105 and checks to see if a source switch trigger has occurred. If no source switch trigger is detected, then the system controller 10 goes to step F106 and determines if a display end trigger has occurred.

The display control trigger signifies an event that cues the system controller 10 in making changes to how images are to be displayed or how the display image data is to be processed, in view of the user's intention or status determined by the user status determination capability 10a.

The source switch trigger means an event that cues the system controller 10 in switching sources of display image data in view of the user's intention or status determined by the user status determination capability 10a, where the display apparatus 1 has a plurality of sources as shown in FIG. 3 or 4.

The display end trigger refers to an event that cues the system controller 10 in causing the display unit 2 to end its display operation and enter the see-through state in view of the user's intention or status determined by the user status determination capability 10a.

The triggers above are detected by the system controller 10 as representative of the user's deliberate operation (any action recognized as an operation) or the user's unconscious operation or status (i.e., user's physical or mental state). How such triggers are recognized and what will be controlled as a result of the detected trigger will be discussed below in more detail.

If a display control trigger is detected, the system controller 10 goes from step F104 to step F107 and controls image display operation. Specifically, the system controller 10 instructs the display control unit 14 to have the display unit 2 give a display reflecting the user's intention or status at that point. Depending on the currently selected source, the system controller may control the image pickup capability block, the storage unit 25 in operation, or the communication unit 26 in operation.

Following the display operation control in step F107, the system controller 10 continues to check for triggers in steps F104, F105 and F106.

If a source switch trigger is detected, the system controller 10 goes from step F105 to step F108 and controls source switching operation. Specifically, the system controller 10 instructs the image input/output control unit 27 and/or the audio input/output control unit 28 to control the newly switched source in operation and to have the display image processing unit 12 and/or audio signal processing unit 16 supplied with the image data and/or audio data coming from the new source.

The source switch control in step F108 illustratively switches the display unit 2 from the state in which the images picked up by the image pickup unit 3 have been displayed, to the state in which the images reproduced from the storage unit 25 are displayed.

Following the source switch control in step F108, the system controller 10 continues to check for triggers in steps F104, F105 and F106.

If a display end trigger is detected, then the system controller 10 goes from step F106 back to step F101 and instructs the display control unit 14 to put the display unit 2 in the see-through state. The currently selected image data source is instructed to end its image feeding operation.

While the display apparatus 1 remains active and is worn by the user, the operation control capability 10b of the system controller 10 carries out the process outlined in FIG. 12.

During the process, four kinds of controls are effected: display start control following detection of the display start trigger, display operation control following detection of the display control trigger, source switch control following detection of the source switch trigger, and control to put the display unit 2 in the see-through state following detection of the display end trigger. Further details of the checks for triggers and specific controls to be executed following trigger detection will be discussed below in reference to FIG. 13 and subsequent figures.

FIGS. 13 through 19 outline typical processes performed by the user status determination capability 10a of the system controller 10. These processes are assumed to be executed in parallel with the process of FIG. 12 performed by the operation control capability 10b. What the parallel execution illustratively signifies is that the process of FIG. 12 being carried out by the system controller 10 is periodically interrupted for detection of triggers by the processes of FIGS. 13 through 19. The programs of these processes may be either embedded in the program of the process in FIG. 12 or furnished separately from the latter program and invoked periodically. That is, the programs may be provided in any suitable form.

Figure 13C:
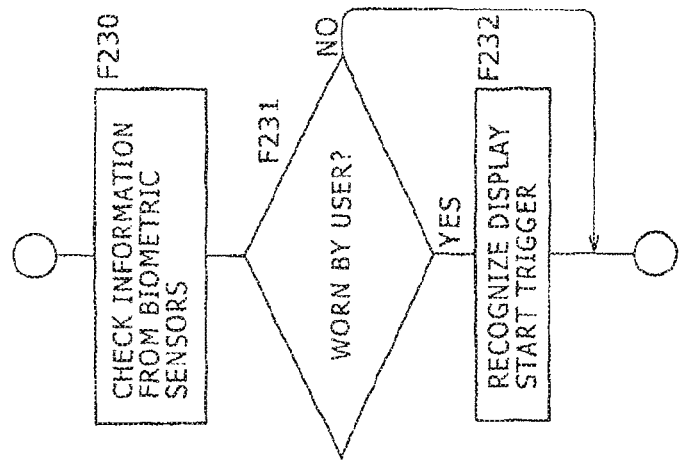
FIGS. 13a-13c are flowcharts of steps constituting typical processes performed by the display apparatus to recognize a display start trigger.
Figure 13B:
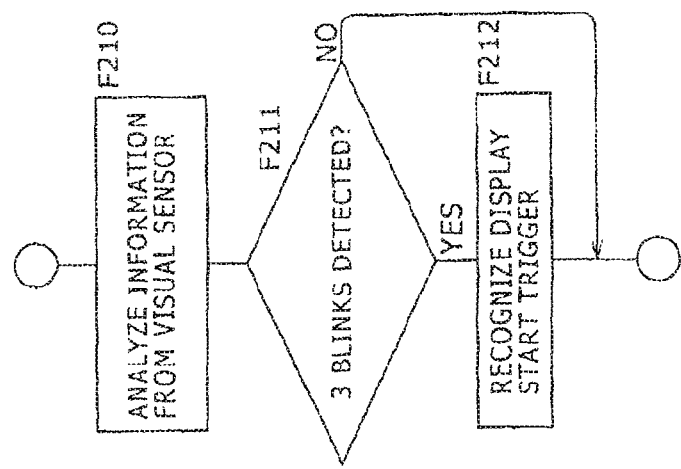
Figure 13A:
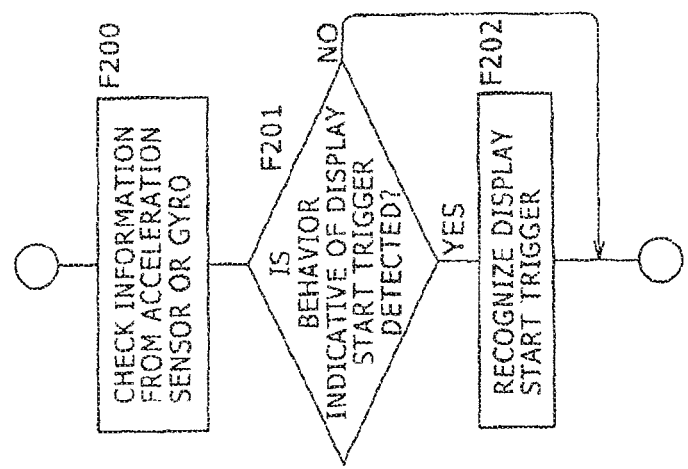

FIG. 13 shows cases in which a display start trigger is detected as a cue to switch from the see-through state to the display state.

(a) and (b) of FIG. 13 indicate cases where the user's behavior is checked for the trigger by which to initiate monitor display.

In step F200 of (a) of FIG. 13, the system controller 10 checks for information detected by the acceleration sensor 20 and/or gyro 21 (acceleration signal, angular velocity signal).

It is assumed that the user's specific movement, such as moving down his head twice, shaking his head right and left in one stroke, or rotating his head in a circular movement, is predetermined as representative of the user's decision to start the display operation. If the detection information from the acceleration sensor 20 and/or the gyro 21 is found to indicate the user's specific moment designating the start of display, then the system controller 10 goes from step F201 to step F202 and recognizes a display start trigger.

With the display start trigger detected in step F202, control of the process in FIG. 12 is passed from step F102 to step F103. In step F103, the system controller 10 controls the display unit 2 to start its image display.

The user's specific behavior to be detected by the acceleration sensor 20 or gyro 21 as representative of the user's decision to start monitor display is not limited to the example cited above. Alternatively, the user may jump, wave his hands, swing his arms, swing his legs, or perform any other bodily motion to gain the same result.

(b) of FIG. 13 shows a case where a display start trigger is determined on the basis of information from the visual sensor 19.

In step F210, the system controller 10 analyzes the information coming from the visual sensor 19. Illustratively, if the visual sensor 19 includes an image pickup device to pick up images of the user's retinal pattern, then the system controller 10 analyzes the image thus acquired by the visual sensor 19.

If the user's three consecutive blinks are predetermined as representative of the user's decision to start the display operation, then the system controller 10 checks for that particular behavior through image analysis. Upon detecting three consecutive blinks of the user, the system controller 10 goes from step F211 to F212 and recognizes a display start trigger.

With the display start trigger detected in step F212, control of the process in FIG. 12 is passed from step F102 to step F103.

In step F103, the system controller 10 controls the display unit 2 to start its image display.

The user's specific behavior to be detected by the visual sensor 19 as representative of the user's decision to start monitor display is not limited to the example cited above. Alternatively, the user may roll the eyes in a circular motion, move the eyes right and left or up and down in two strokes, or do any other suitable eye movement to gain the same result.

(c) of FIG. 13 shows a case in which the user's act of wearing the display apparatus 1 itself is interpreted as a display start trigger.

In step F230, the system controller 10 checks for such information as brain wave, heart rate, and galvanic skin reflex from the biometric sensors 22.

In step F231, the system controller 10 checks the information from the biometric sensors 22 to determine whether the user is wearing the display apparatus 1. The fact that biometric information starts getting acquired by the biometric sensors 22 is interpreted as the user starting to wear the display apparatus 1.

Upon detecting the user wearing the display apparatus 1, the system controller 10 goes from step F231 to step F232 and recognizes a display start trigger. With the display start trigger detected in step F232, the system controller 10 reaches step F103 in FIG. 12 and carries out the display start control.

Whether or not the user is wearing the display apparatus 1 is determined as described above on the basis of the vital reaction information from the biometric sensors 22.

As soon any of such findings as the pulse rate, brain wave, and galvanic skin reflex starts getting detected, the display start trigger is recognized. The user's act of wearing the display apparatus 1 thus prompts the system controller 10 to start the display operation.

It is also possible to start display control when the display apparatus 1 is worn not by any user but by a particular user. The user's retinal pattern detected by the visual sensor 19 or the detection signal from the biometric sensors 22 may be used to identify individual users. Where the retinal patterns or specific biometric information about expected users is registered in advance, the system controller 10 may determine which user is currently wearing the display apparatus 1 in accordance with the incoming information.

Specifically, when a certain user wears the display apparatus 1, the system controller 10 authenticates the user's identity. If a particular user's identity is recognized, then the system controller 10 detects the display start trigger and performs display start control accordingly.

It is also possible to detect the display start trigger by interpreting the user's diverse unconscious behavior or physical status.

For example, a sudden shift in the user's line of sight in the information coming from the visual sensor 19 may be interpreted as a display start trigger. The display start trigger may be recognized alternatively by use of other information from the visual sensor 19 or on the basis of input sounds from the audio input unit 6.

When an image is displayed by the display unit 2 in response to the display start trigger as described above, a see-through state area AR1 may be left intact on the screen of the display unit 2 while another area AR2 is arranged to display the image being picked up, as shown in (b) of FIG. 9.

Although not shown in FIG. 12, arrangements may be made to recognize a power-on trigger from the user starting to wear the display apparatus 1 as shown in (c) of FIG. 13. In this case, the system controller 10 turns on the display apparatus 1 upon detection of the apparatus 1 getting worn by the user.

Conversely, the system controller 10 may switch off the display apparatus 1 when detecting the apparatus 1 getting unmounted by the user.

Described below in reference to FIGS. 14 through 17 are typical processes carried out as a result of the recognition of a display control trigger in step F104 of FIG. 12.

Figure 14:
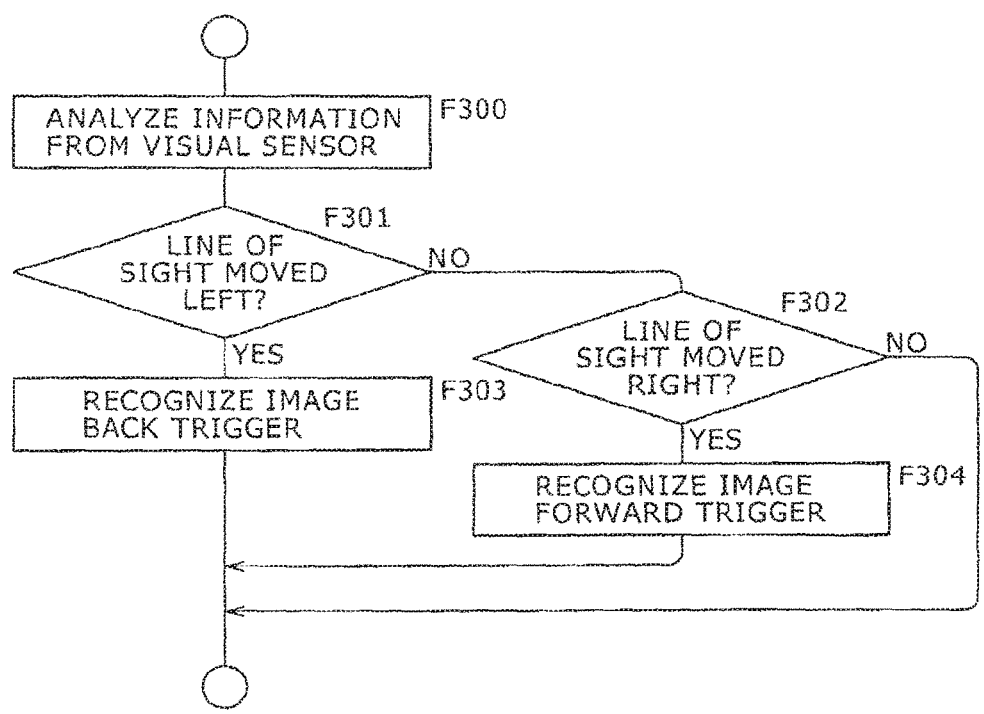
FIG. 14 is a flowchart of steps constituting a typical process performed by the display apparatus to recognize display control triggers.

FIG. 14 is a flowchart of steps constituting the typical process for moving the displayed page or its highlighted portion forward and backward in response to the user's line of sight movements.

In step F300 of FIG. 14, the system controller 10 analyzes the information coming from the visual sensor 19. If the visual sensor 19 includes an image pickup unit to take pictures of the user's eyes, then the system controller 10 analyzes the eye image thus acquired.

If the user's line of sight is found moving leftward, then the system controller 10 goes from step F301 to step F303 and recognizes an image-back trigger.

If the user's line of sight is found moving rightward, then the system controller 10 goes from step F302 to step F304 and recognizes an image-forward trigger.

In any of the cases above, control of the process in FIG. 12 is passed from step F104 to step F107 and the system controller 10 performs display image forward/backward control. If the storage unit 25 is set to be the source, with the reproduced image displayed as shown in (c) of FIG. 6 or (c) of FIG. 8, then the system controller 10 controls the display image processing unit 12 and storage unit 25 in such a manner as to move forward or back the current page or its highlighted portion.

Although the example above was shown to utilize detection of the user's line of sight moving right or left, this is not limitative of the present invention. Alternatively, the user's line of sight moving up or down may be detected and interpreted as a screen scroll trigger, whereby the display screen may be scrolled as desired by the user.

Figure 15:
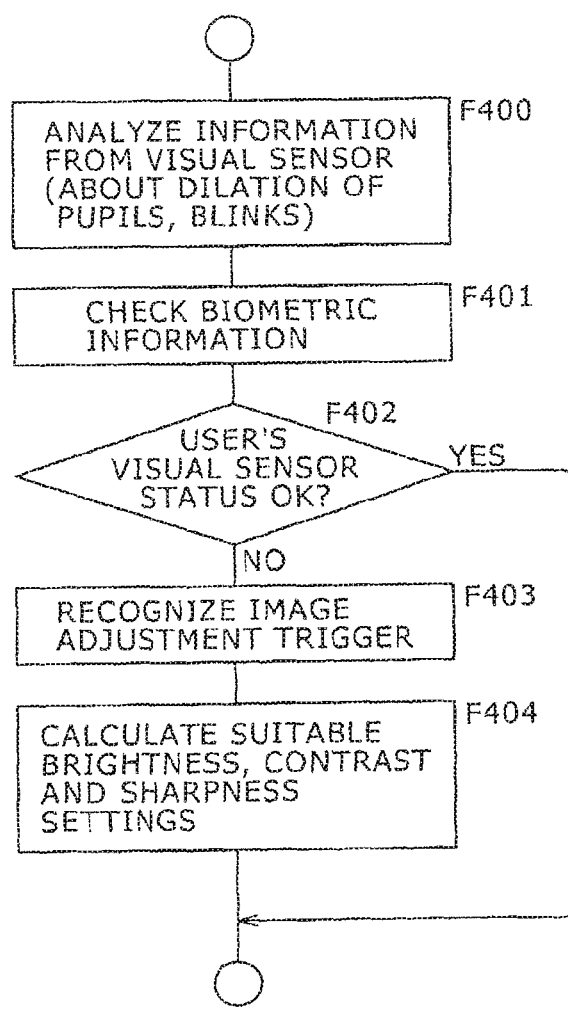
FIG. 15 is a flowchart of steps constituting a typical process performed by the display apparatus to recognize another display control trigger.

FIG. 15 is a flowchart of steps constituting the typical process for controlling display status based on the user's pleasant and unpleasant sensations.

In step F400 of FIG. 15, the system controller 10 analyzes information coming from the visual sensor 19 to detect the user's pupil dilation and blinks (number of blinks per unit time).

In step F401, the system controller 10 checks biometric information such as the brain wave, heart rate, perspiration, and blood pressure coming from the biometric sensors 22.

Given such information from the visual sensor 19 and biometric sensors 22, the system controller 10 checks to determine whether the user is in a comfortable state with regard to the image being displayed by the display unit 2.

If the user's state of visual perception is found to be uncomfortable, then the system controller 10 goes from step F402 to step F403 and recognizes an image adjustment trigger. The system controller 10 then goes to step F404 and calculates modified settings deemed to bring about comfort to the user in his or her situation, such as adjusted settings of display brightness, contrast, and sharpness.

Following steps F403 and F404, control of the process in FIG. 12 by the system controller 10 is passed from F104 to step F107. In this case, the system controller 10 instructs the display image processing unit 12 to carry out such processes as brightness level adjustment, contrast adjustment, and sharpness control. The processing adjusts the quality of the image displayed by the display unit 2 so that the image will appear more comfortable to the user than before.

For example, the user's state of visual perception may deteriorate by eyestrain or as a result of aberrant ambient brightness against which the image picked up by the image pickup capability block is being displayed. In such a case, the above processing corrects the situation and allows the user to restore a pleasant state of visual perception. Illustratively, a dimmed unclear image such as one shown in (a) of FIG. 11 may be replaced by a clearer image indicated in (b) of FIG. 11. In case of eyestrain on the user's part, the currently displayed image may be turned from its hard contrast state into an image of softer contrast.

Figure 16:
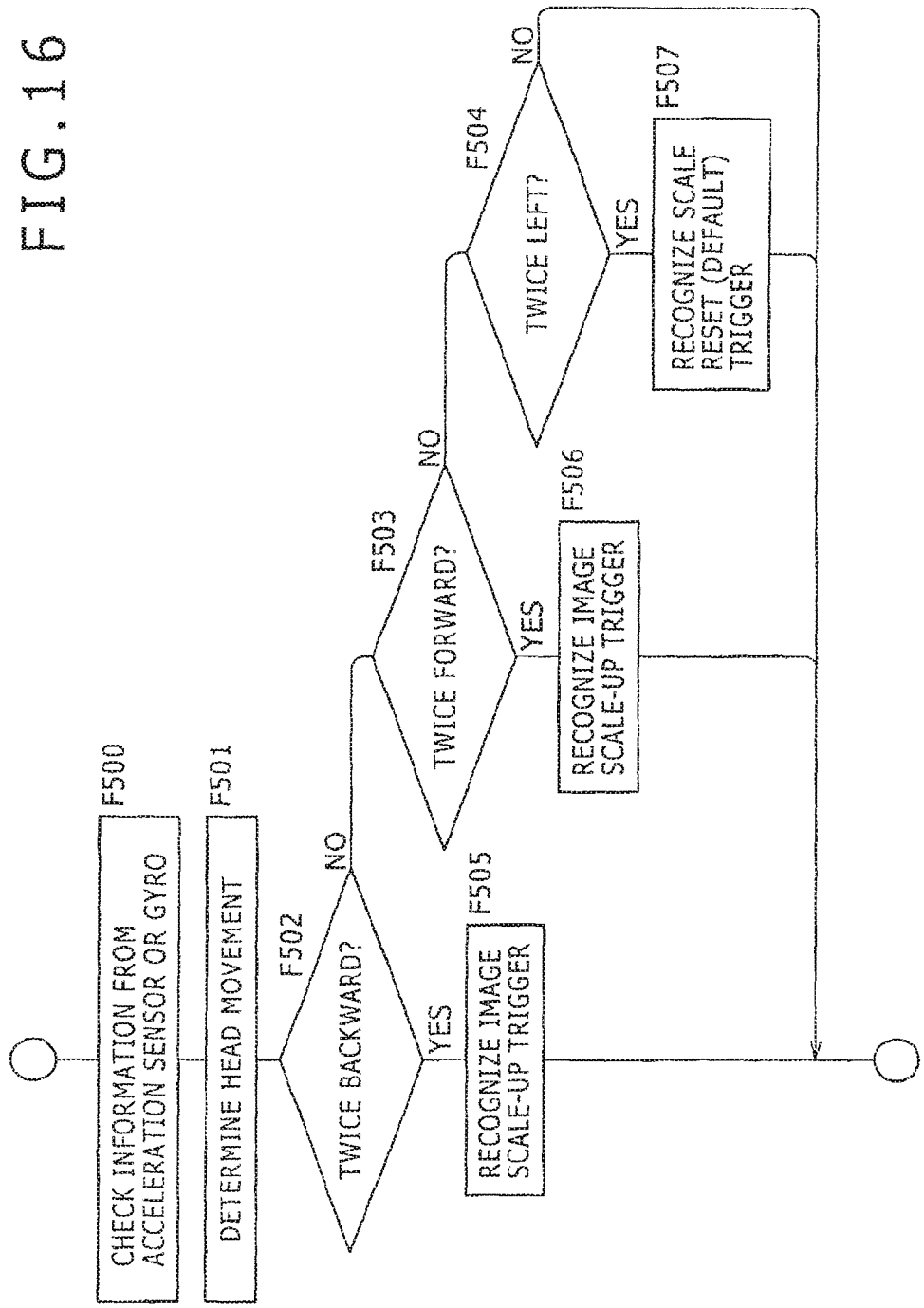
FIG. 16 is a flowchart of steps constituting a typical process performed by the display apparatus to recognize other display control triggers.

FIG. 16 is a flowchart of steps constituting the typical process for interpreting movements of the user's head as meaningful operations.

In step F500, the system controller 10 checks for information detected by the acceleration sensor 20 and/or gyro 21 (acceleration signal, angular velocity signal). In step F501, the system controller 10 determines the movement of the user's head. For example, checks are made to see if the user's head has moved backward twice, forward twice, or leftward twice.

If the user's head is found to have moved backward twice, then the system controller 10 goes from step F502 to step F505 and recognizes an image scale-up trigger.

In this case, control of the process in FIG. 12 by the system controller 10 is passed from step F104 to step F107, and the system controller 10 instructs the display image processing unit 12 to perform an image scale-up process. This in turn causes the display unit 2 to display a scaled-up image such as one in (b) of FIG. 10.

If the user's head is found to have moved forward twice, then the system controller 10 goes from step F503 to step F506 and recognizes an image scale-down trigger. In this case, control of the process in FIG. 12 by the system controller 10 is also passed from step F104 to step F107, and the system controller 10 instructs the display image processing unit 12 to perform an image scale-down process. This in turn causes the display unit 2 to display a scaled-down image.

If the user's head is found to have moved leftward twice, then the system controller 10 goes from step F504 to step F507 and recognizes an image scale reset (default) trigger. In this case, too, control of the process in FIG. 12 by the system controller 10 is passed from step F104 to step F107, and the system controller 10 instructs the display image processing unit 12 to perform a scale reset process. This in turn causes the display unit 2 to display an image of the default scale.

Figure 17:
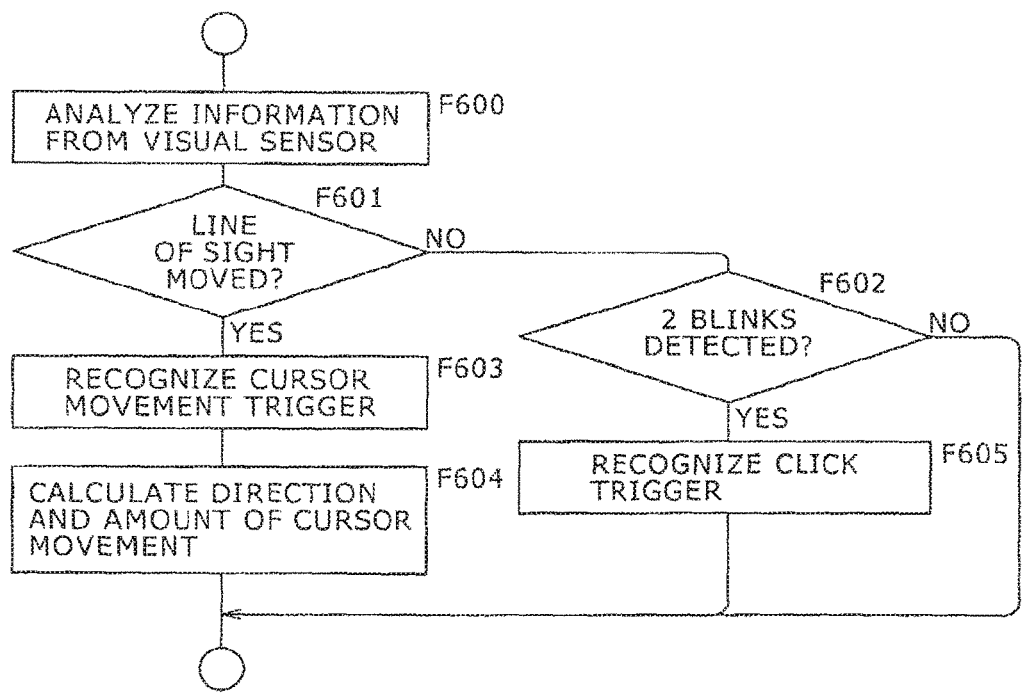
FIG. 17 is a flowchart of steps constituting a typical process performed by the display apparatus to recognize other display control triggers.

FIG. 17 is a flowchart of steps constituting the typical process for recognizing a trigger for making input operations on the display screen based on the information from the visual sensor 19.

In step F600 of FIG. 17, the system controller 10 analyzes the information coming from the visual sensor 19. If the visual sensor 19 includes an image pickup unit to take pictures of the user's eyes, then the system controller 10 analyzes the eye image thus acquired and checks for movements of the user's line of sight or for the user's blinks while looking at the display unit 2.

Upon detecting a movement of the user's line of light, the system controller 10 goes from step F601 to step F603 and recognizes a trigger for moving the cursor (i.e., onscreen pointer) on the display screen. In step F604, the system controller 10 calculates the direction and amount of the cursor movement over the screen based on the direction and mount of the detected line-of-sight movement.

In this case, the system controller 10 reaches step F107 in FIG. 12 and instructs the display image processing unit 12 to move the cursor as calculated. Illustratively, if the image such as one in (b) and (c) of FIG. 8 is being displayed, the cursor is moved on that display screen.

Upon detecting the user's two consecutive blinks, the system controller 10 goes from step F602 to step F605 and recognizes a trigger for a click operation. In this case, the system controller 10 reaches step F107 in FIG. 12 and performs a control process corresponding to the click. Illustratively, if the click is found to be associated with a reproduced image coming from the storage unit 25, the system controller 10 controls the storage unit 25 in its reproducing operation in a manner reflecting the click operation; if the click is found to be made on the image being received by the communication unit 26, the system controller 10 sends to the connected external apparatus the cursor position and click-invoked operation information in effect at the moment.

The processing above allows the user's eye movements to be used as triggers commensurate with the operations of a mouse attached to a typical computer system. When a video game image such as one in (b) of FIG. 6 is being displayed, the user's line of sight and blinks may be detected and utilized as the user's operations reacting to the game in progress.

The processes in FIGS. 14, 15, 16 and 17 were shown to control how images are to be displayed onscreen, how the image data for display is to be processed, or how operations are to be carried out on the display screen in response to the user's deliberate or unconscious operations or physical status. However, the examples cited above are only for illustration purposes; there may be many other examples in which display control triggers are detected and controls are carried out accordingly.

A display control trigger can be recognized whenever predetermined conditions are found to be met following detection of the user's behavior and physical status from diverse information coming from the visual sensor 19, acceleration sensor 20, gyro 21, and biometric sensors 22.

When a display control trigger is recognized under diverse conditions, the display image processing unit 12 may be operated to execute scale-up/scale-down control; brightness, contrast and sharpness adjustment; control on image effects including pixelated mosaic effect, images in reverse video, and soft-focus images; and control on split-screen display and strobe-induced image display, in accordance with the user's behavior and physical status in effect.

If the image pickup capability block is selected as the source, with picked-up images displayed by the display unit 2, then the image pickup unit 3 and image pickup signal processing unit 15 may be operated to execute zoom control between telephoto and wide-angle shot settings, imaging sensitivity control, switchover between imaging frame rates, and changes to infrared or ultraviolet imaging sensitivity settings.

If the reproduced image from the storage unit 25 or the received image from the communication unit 26 is displayed by the display unit 2, then diverse display control triggers may be recognized and the storage unit 25 or communication unit 26 may be operated accordingly. That is, the operations may deal with variable speed reproduction controls such as fast-forward/fast-rewind, instant access to desired positions, frame-by-frame feed, slow reproduction, and pause; page feed, page scroll, shift of a highlighted portion within a list display, cursor movement, decision-finalizing operation, and video game actions.

In other words, the conditions under which to detect display control triggers may be associated with the corresponding control operations in a large number of combinations.

When onscreen displays on the display unit 2 are to be changed in response to the display control trigger as described above, the wider area AR1 may be left unchanged in its see-through state or normal display state while the smaller area AR2 is arranged to display images in a different form, as shown in (b) of FIG. 9. Obviously, it is also possible to display an image reflecting the display control trigger in the wider area AR1. As another alternative, the screen may be divided into equal parts in which the normal pickup image and the image corresponding to the display control trigger are displayed as needed.

The foregoing description given in reference to FIGS. 14 through 18 was about how different examples of the display control trigger are recognized and how they are handled through appropriate controls. Similarly, various examples of the source switch trigger to be detected in step F105 of FIG. 12 may be conceived.

That is, the user's deliberate actions as well as his unconscious behavior and physical status may be detected from the information supplied by the visual sensor 19, acceleration sensor 20, gyro 21, and biometric sensors 22. When a particular condition is found to be met, the presence of a source switch trigger may be detected.

With the source switch trigger thus recognized, the system controller 10 may go to step F108 in FIG. 12 and switch the sources that supply image data to the display image processing unit 12.

Figure 18A:
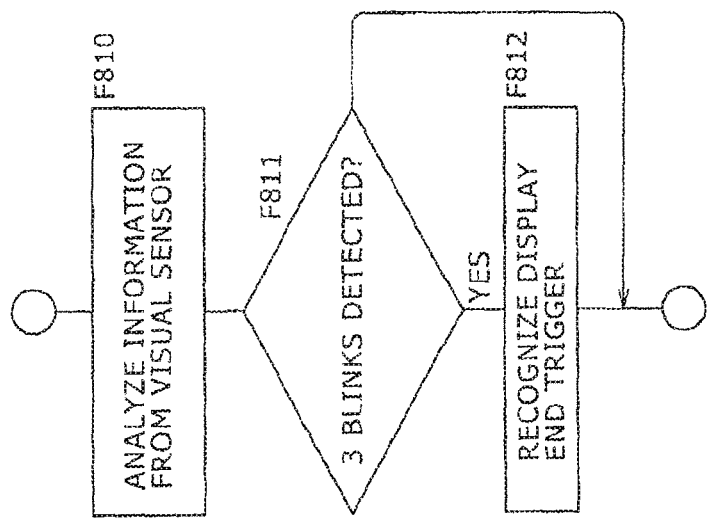
FIGS. 18a-18b are flowcharts of steps constituting typical processes performed by the display apparatus to recognize a display end trigger.
Figure 18B:
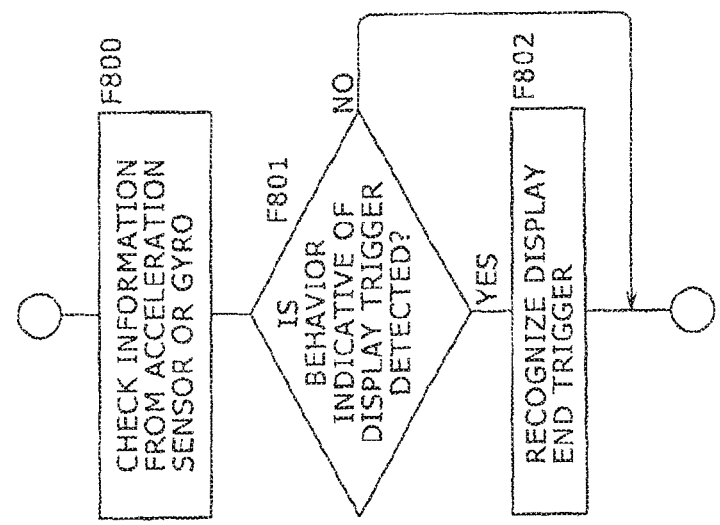
Figure 19B:
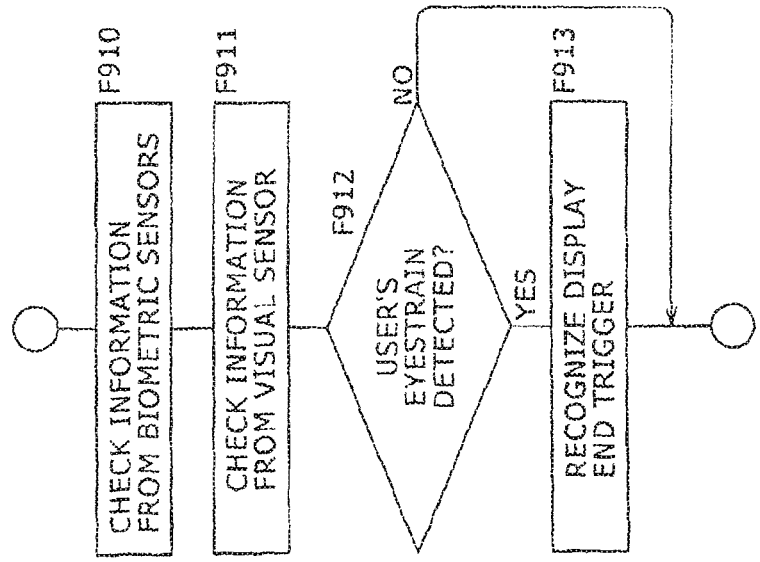
FIGS. 19a-19b are flowcharts of steps constituting other typical processes performed by the display apparatus to recognize the display end trigger.
Figure 19A:
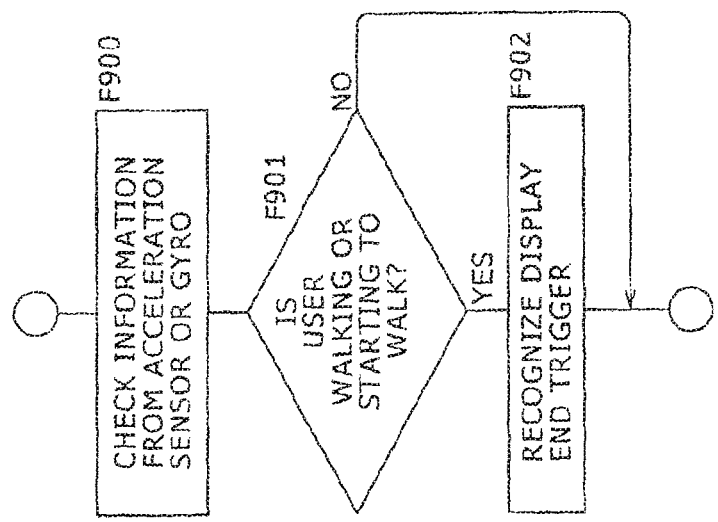

Described below in reference to FIGS. 18 and 19 are examples of the display end trigger to be detected in step F106 of FIG. 12, the trigger giving a cue to switch from the image display state to the see-through state.

(a) of FIG. 18 is a flowchart of steps constituting a typical process for ending the display operation based on the user's deliberate behavior.

In step F800 of (a) of FIG. 18, the system controller 10 checks the information detected by the acceleration sensor 20 and gyro 21 in order to determine the user's head movement and whole body movement.

Upon detecting the user's particular behavior designating the desire to end monitor display, the system controller 10 goes from step F801 to step F802 and recognizes a display end trigger.

After step F802, control of the process in FIG. 12 by the system controller 10 is passed from step F106 to step F101. In this case, the system controller 10 instructs the display control unit 14 to effect switchover to the see-through state. This puts the display unit 2 back into the see-through state as shown in (a) of FIG. 5.

(b) of FIG. 18 is a flowchart of steps constituting another typical process for ending the display operation based on the user's deliberate behavior.

In step F810 of (b) of FIG. 18, the system controller 10 analyzes information coming from the visual sensor 19. If the user's three consecutive blinks were preset as an operation to be made by the user to designate an end of display, then the system controller 10 checks for this behavior through image analysis.

Upon detecting three consecutive blinks on the user's part, the system controller goes from step F811 to step F812 and recognizes a display end trigger.

After step F812, control of the process in FIG. 12 by the system controller 10 is passed from step F106 to step F101, and the system controller 10 instructs the display control unit 14 to effect switchover to the see-through state. The display unit 2 is then placed back into the see-through state as shown in (a) of FIG. 5.

Where the user's desire to bring about the see-through state is expressed by behavior as outlined in (a) and (b) of FIG. 18, the control operation reflecting the user's intention is carried out. Obviously, it is possible to conceive many other kinds of behavior on the user's part expressing the user's desire to put the see-through state into effect.

(a) of FIG. 19 is a flowchart of steps constituting a typical process for automatically switching back to the see-through state in response to the user's movement (i.e., an action performed unconsciously as an actuating operation).

In step F900 of (a) of FIG. 19, the system controller 10 checks the information detected by the acceleration sensor 20 and gyro 21 in order to determine the user's whole body movement. In particular, the system controller 10 checks to determine whether the user is at rest, walking, or running.

Upon detecting the user starting to walk or run, the system control goes from step F901 to step F902 and recognizes that a display end trigger has occurred.

After step F902, control of the process in FIG. 12 by the system controller 10 is passed from step F106 to step F101, and the system controller 10 instructs the display control unit 14 to effect switchover to the see-through state. In turn, the display unit 2 is placed back into the see-through state as shown in (a) of FIG. 5.

Interpreting the user's walking or running state as the cue to bring back the see-through state is desirable in terms of ensuring the user's safety.

However, the switch back to the see-through state on cue is not limitative of the invention. Alternatively, upon detection of the user's walking or running state, monitor display may be switched to the normal pickup image equivalent to the see-through state as shown in (b) of FIG. 5.

(b) of FIG. 19 is a flowchart of steps constituting a typical process for automatically bringing back the see-through state in response to the user's physical status.

In step F910 of (b) of FIG. 19, the system controller 10 checks such information from the biometric sensors 22 as the user's brain wave, heart rate, perspiration, and blood pressure.

In step F911, the system controller 10 analyses information from the visual sensor 19 to check the user's pupil dilation and blinks (number of blinks per unit time).

On the basis of the information coming from the biometric sensors 22 and visual sensor 19, the system controller 10 checks to determine whether the user's eyes are unduly strained.

Upon detecting the user's eyestrain, the system controller 10 goes from step F912 to step F913 and recognizes that a display end trigger has occurred.

After step F913, control of the process in FIG. 12 by the system controller 10 is passed from step F106 to step F101, and the system controller 10 instructs the display control unit 14 to effect switchover to the see-through state. Illustratively, display of the pickup image on the monitor screen at enhanced infrared imaging sensitivity is terminated, and the display unit 2 is placed back into the see-through state.

When the display operation of the display unit 2 is brought to an end in response to the user's physical status such as eyestrain, the display apparatus 1 can be used in a manner minimizing the burdens on the user's physical condition.

6. Effects, Variations and Extensions of the Embodiments

The preferred embodiment of the present invention has been described above. The description has focused, among others, on the display unit 2 which is part of an eyeglass-like or head mount-type wearable unit of the display apparatus 1 and which displays images immediately before the user's eyes. With this setup, information about the user's movements and physical status is used as the basis for determining the user's intentions and biometric status. The result of what has been determined is in turn used to control display-related operations, whereby a suitable display is implemented corresponding to the user's intentions and status with little operational effort on the user's part. The inventive display apparatus 1 thus provides excellent usability and offers the user varieties of visual experiences.

With the display unit 2 placed in the transparent or translucent see-through state through control of its transmittance, the display apparatus 1 when worn by the user does not bother him in his daily pursuits. The benefits of the inventive display apparatus 1 can be enjoyed by the user while leading ordinary life.

In the foregoing description, emphasis was placed on how to control display operations. Alternatively, the user's behavior and biometric status may be used as the basis for controlling the switchover between power-on, power-off, and standby state of the apparatus and for adjusting the volume and quality of sounds being output by the audio output unit 5. Illustratively, sound level control may be effected by checking the information from the biometric sensors 22 to see how comfortable the user is at present.

The display apparatus 1 may incorporate a character recognition block that recognizes characters in images, and a speech synthesis block that performs speech synthesizing processes. With such modifications in place, the character recognition block recognizes any characters that may be found included in the images that have been picked up, reproduced, or received. Given the recognized characters, the speech synthesis block generates read-aloud voice signals causing the audio output unit 5 to read the characters aloud.

The appearance and structures of the display apparatus 1 are not limited to those shown in FIGS. 1, 3 and 4. Many other variations and modifications are conceivable.

Although the display apparatus 1 was described as mountable on the eyeglass-like or head mount-type wearable unit, this is not limitative of the invention. The display apparatus 1 according to the invention need only be structured to give display immediately before the user's eyes. Illustratively, the inventive apparatus may be of a headphone type, a neck band type, a ear-hook type, or any other wearable type. As other alternatives, the display apparatus may be worn by the user in a manner attached to the user's eyeglasses, visor, headphones, or other daily-worn accessories with a clip or like fittings.

The invention claimed is:

1. A display apparatus comprising:
a display that displays an image and is positioned in front of an eye of a user;
a biometric sensor that detects biometric information of the user;
a visual sensor that detects an action or condition of the eye of the user, wherein the visual sensor is distinct from the biometric sensor; and
a controller circuitry configured to determine an eyestrain of the user based on the biometric information of the user sensed by the biometric sensor and the action or condition of the eye of the user detected by the visual sensor, and to control the display based on the determined eyestrain of the user.

2. The display apparatus according to claim 1, wherein:
the controller circuitry is further configured to detect a display end trigger condition based on the determined eyestrain of the user; and
the controller circuitry controls the display to stop displaying the image in accordance with the detected display end trigger condition.

3. The display apparatus according to claim 1, wherein:
the biometric sensor is configured to detect, as the biometric information of the user, a heart rate, pulse rate, perspiration, brain wave, galvanic skin reflex, blood pressure, body temperature, or breathing rate of the user.

4. The display apparatus according to claim 3, wherein:
the biometric sensor is configured to detect the brain wave of the user including at least one of an alpha wave, a beta wave, a theta wave, and a gamma wave.

5. The display apparatus according to claim 1, wherein:
the controller circuitry is further configured to control the display, based on the determined eyestrain of the user, to switch between a display state and a seethrough state, said see-through state being a state in which said display remains either transparent or translucent, and said display state being a state in which said display displays the image.

6. The display apparatus according to claim 1, wherein:
the visual sensor is configured to detect, as the action or condition of the eye of the user, a line of sight, a focal distance, a pupil dilation, a retinal pattern, or number of blinks per unit time of the eye of the user.

7. The display apparatus according to claim 1, wherein:
the controller circuitry is further configured to determine if the user is in a tense state, an excited state, a calm state, a sleepy state, a comfortable state, or an uncomfortable state based on the biometric information of the user detected by the biometric sensor.

8. The display apparatus according to claim 1, wherein:
the controller circuitry is further configured to determine if the display apparatus is currently being worn by the user based on the biometric information of the user detected by the biometric sensor.

9. The display apparatus according to claim 1, wherein:
the controller circuitry is further configured to authenticate a user's identity based on the biometric information of the user detected by the biometric sensor.

10. The display apparatus according to claim 1, further comprising:

a head mount frame that supports the display in front of the eye of the user, wherein the biometric sensor is arranged inside the head mount frame.

11. The display apparatus according to claim 1, further comprising:
a head mount frame that supports the display in front of the eye of the user, wherein the biometric sensor is arranged on the user's body independent from the head mount frame.

12. The display apparatus according to claim 1, further comprising:
an audio output device configured to output audio; and
based on the at least one of the biometric information of the user sensed by the biometric sensor and the action or condition of the eye of the user detected by the visual sensor, the controller circuitry is further configured to switch the display between a power-off, a power-on, and a standby-state, and to adjust a volume and a quality of a sound level being output by the audio output device.

13. A display method comprising:
displaying an image on a display positioned in front of an eye of a user;
detecting biometric information of the user using a biometric sensor;
detecting an action or condition of the eye of the user using a visual sensor, wherein the visual sensor is distinct from the biometric sensor;
determining an eyestrain of the user based on the biometric information and the action or condition of the eye of the user; and
controlling the display based on the determined eyestrain of the user.

14. The method according to claim 13, further comprising:
detecting a display end trigger condition based on the determined eyestrain of the user; and
controlling the display to stop displaying the image in accordance with the detected display end trigger condition.

15. The method according to claim 13, further comprising:
detecting a heart rate, pulse rate, perspiration, brain wave, galvanic skin reflex, blood pressure, body temperature, or breathing rate of the user as the biometric information of the user.

16. The method according to claim 14, further comprising:
detecting the brain wave of the user including at least one of an alpha wave, a beta wave, a theta wave, and a gamma wave.

17. The method according to claim 13, further comprising:
controlling the display, based on the determined eyestrain of the user, to switch between a display state and a seethrough state, said see-through state being a state in which said display remains either transparent or translucent, and said display state being a state in which said display displays the image.

18. The method according to claim 13, further comprising:
detecting, as the action or condition of the eye of the user, a line of sight, a focal distance, a pupil dilation, a retinal pattern, or number of blinks per unit time of the eye of the user.

19. The method according to claim 13, further comprising:
determining if the user is in a tense state, an excited state, a calm state, a sleepy state, a comfortable state, or an uncomfortable state based on the biometric information of the user.

20. The method according to claim 13, further comprising:
determining if the display apparatus is currently being worn by the user based on the biometric information of the user.

21. The method according to claim 13, further comprising:
authenticating a user's identity based on the biometric information of the user.

22. The method according to claim 13, further comprising:
switching the display between a power-off, a power-on, and a standby-state, and adjusting a volume and a quality of a sound level being output by an audio output device based on the at least one of the biometric information of the user and the action or condition of the eye of the user.

23. The method according to claim 13, wherein the determining of the eyestrain of the user is based on the biometric information and the action or condition of the eye of the user.

* * * * *